US009157072B2

(12) United States Patent
Wu et al.

(10) Patent No.: US 9,157,072 B2
(45) Date of Patent: Oct. 13, 2015

(54) HYBRID BACULOVIRUS HAVING THE CAPABILITY OF INFECTING AT LEAST THREE INSECT HOSTS AND USES THEREOF

(71) Applicant: Chung Yuan Christian University, Jongli, Taoyuan county (TW)

(72) Inventors: Tzong-Yuan Wu, Panchiao (TW); Mean-Shine Chen, Jhongli (TW); Chao-Yi Teng, Jhongli (TW); Ying-Ju Chen, Yanpu Village (TW)

(73) Assignee: CHUNG YUAN CHRISTIAN UNIVERSITY, Jhongli, Taoyuan County (TW)

( * ) Notice: Subject to any disclaimer, the term of this patent is extended or adjusted under 35 U.S.C. 154(b) by 0 days.

(21) Appl. No.: 14/277,892

(22) Filed: May 15, 2014

(65) Prior Publication Data

US 2015/0252333 A1 Sep. 10, 2015

Related U.S. Application Data

(63) Continuation-in-part of application No. 14/203,489, filed on Mar. 10, 2014.

(51) Int. Cl.
*C12N 7/00* (2006.01)

(52) U.S. Cl.
CPC ........ *C12N 7/00* (2013.01); *C12N 2710/14121* (2013.01)

(58) Field of Classification Search
None
See application file for complete search history.

(56) References Cited

PUBLICATIONS

U.S. Appl. No. 14/203,489, filed Mar. 10, 2014, Wu, et. al.
Betting et al., "Enhanced immune stimulation by a therapeutic lymphoma tumor antigen vaccine produced in insect cells involves mannose receptor targeting to antigen presenting cells". 2009 Vaccine 27 (2): 250-9.
Zerbino DR et al. In "Velvet: algorithms for de novo short read assembly using de Bruijn graphs" (Genome research 2008, 18 (5): 821-829).
Chen YR et al. In "Genomic and host range studies of Maruca vitrata nucleopolyhedrovirus" (J. General Virology 2008, 89: 2315-2330).
Liao CH et al. "Study on the Production of Foreign Proteins in Silkworm (*Bombyx mori* L.)" Bulletin of Miaoli District Agricultural Research and Extension Station 2011, 02: 01-12.

*Primary Examiner* — Jennifer Dunston
*Assistant Examiner* — Addison D Ault
(74) *Attorney, Agent, or Firm* — Muncy, Geissler, Olds & Lowe, P.C.

(57) ABSTRACT

Disclosed herein is an *Autographa californica* multiple nucleopolyhedrovirus (AcMNPV) based hybrid baculovirus and its uses thereof. The AcMNPV based hybrid baculovirus is capable of infecting different hosts, and comprises *Bombyx mori* nuclear polyhedrosis virus (BmNPV) genes of lef9, vlf1, p6.9, and vp80; *Maruca vitrata* multiple nucleopolyhedrovirus (MaviMNPV) genes of lef2, orf1629, and pe38; and AcMNPV/BmNPV/MaviMNPV-hybrid genes of pk1, lef8, DNA pol, GP41, helicase, orf94, VP1054, orf65, lef4, lef5, and orf99. The AcMNPV based hybrid baculovirus is therefore useful as a bio-tool or bio-insecticide for its capability of delivering genes for production or expression of toxic proteins in at least three different insect hosts.

19 Claims, 9 Drawing Sheets
(9 of 9 Drawing Sheet(s) Filed in Color)

HYBRID BACULOVIRUS HAVING THE CAPABILITY OF INFECTING AT LEAST THREE INSECT HOSTS AND USES THEREOF

CROSS-REFERENCE TO RELATED APPLICATIONS

This is a continuation-in-part of U.S. patent application Ser. No. 14/203,489, filed Mar. 10, 2014.

BACKGROUND OF THE INVENTION

1. Field of the Invention

The present disclosure relates to a hybrid baculovirus. Specifically, the present disclosure relates to novel *Autographa californica* multiple nucleopolyhedrovirus (AcMNPV) based hybrid baculovirus capable of infecting at least three different hosts.

2. Description of Related Art

The baculoviruses have been divided into four genera: Alphabaculovirus (nucleopolyhedroviruses (NPVs) isolated from *Lepidoptera*), Betabaculoviruses (granuloviruses (GV) isolated form *Lepidoptera*), Gammabaculoviruses (NPVs isolated from hymenoptera) and Deltabaculoviruses (NPVs isolated from Dipter). While GVs contain only one nucleocapsid per envelope, NPVs contain either single (SNPV) or multiple (MNPV) nucleocapsids per envelope. The enveloped virions are further occluded in granulin matrix in GVs and polyhedrin in NPVs.

Baculoviruses have a restricted range of hosts that they can infect, which is typically restricted to a limited number of closely related insect species. Since baculoviruses are not harmful to humans, they are considered to be a safe option as biological agents to produce exogenous proteins in baculoviruses-permissive insect cells or larvae. For example, proteins produced by baculoviruses have been used as therapeutic cancer vaccines with several immunologic advantages over proteins derived from mammalian sources (Betting et al., “Enhanced immune stimulation by a therapeutic lymphoma tumor antigen vaccine produced in insect cells involves mannose receptor targeting to antigen presenting cells”. *Vaccine* 2009, 27 (2): 250-9).

What would be useful for the application of baculoviruses in industry or in agriculture, would be to devise improved baculoviruses with a wider host range that they can infect, hence allowing baculoviruses carrying genes of proteins of interest, to be used in mass protein production method; or as bioinsecticides, for a wider range of insect hosts may be reached.

SUMMARY

The present disclosure provides a novel AcMNPV based hybrid baculovirus capable of infecting at least three different insect hosts and its uses for producing exogenous proteins such as toxic proteins in these hosts. Accordingly, the novel AcMNPV hybrid baculovirus is useful as a cross host bioinsecticide, for at least three different insect hosts are permissive to this novel AcMNPV hybrid baculovirus.

It is the first object of the present disclosure to provide an *Autographa californica* multiple nucleopolyhedrovirus (AcMNPV) based hybrid baculovirus capable of infecting at least three different hosts. The AcMNPV based hybrid baculovirus comprises at least *Bombyx mori* nuclear polyhedrosis virus (BmNPV) genes of lef9, vlf1, p6.9, and vp80; *Maruca vitrata* multiple nucleopolyhedrovirus (MaviMNPV) genes of lef2, orf1629, and pe38; and AcMNPV/BmNPV/MaviMNPV-hybrid genes of pk1 (SEQ ID NO: 1), lef8 (SEQ ID NO: 2), DNA pol (SEQ ID NO: 3), GP41 (SEQ ID NO: 4), helicase (SEQ ID NO: 5), orf94 (SEQ ID NO: 6), VP1054 (SEQ ID NO: 7), orf65 (SEQ ID NO: 8), lef4 (SEQ ID NO: 9), lef5 (SEQ ID NO: 10), and orf99 (SEQ ID NO: 11).

In some optional embodiments, the AcMNPV based hybrid baculovirus may further include a first nucleic acid encoding a first fluorescent protein, which is any of green fluorescence protein (GFP), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), or *Clavularia* fluorescent protein (cFP).

The AcMNPV based hybrid baculovirus is capable of infecting AcMNPV-permissive cells or insect larvae, BmNPV-permissive cells or insect larvae, as well as MaviMNPV-permissive cells or insect larvae. According to some examples, the AcMNPV-permissive cells may be any of *S. furgiperda* IPBL-9(Sf9), Sf21, or High-five (Hi-5) cells; and the AcMNPV-permissive insect larvae are *Trichoplusia ni* or *Spodoptera frugiperda*. In another example, the BmNPV-permissive cells are BmN cells; and the BmNPV-permissive insect larvae are *Bombyx mori*. In still another example, the MaviMNPV-permissive cells are NTU-MV532 cells; and the MaviMNPV-permissive insect larvae are *Maruca Vitrata*.

It is the second object of the present disclosure to provide a method of producing an exogenous protein in an insect host by use of the novel hybrid baculovirus of the present disclosure. The method includes steps of:

(a) co-transfecting the first insect host with the AcMNPV based hybrid baculovirus having a first nucleic acid encoding a first fluorescent protein of the present disclosure and a transfer vector to allow the recombination between the AcMNPV based hybrid baculovirus and the transfer vector in the co-transfected first insect host, wherein the transfer vector comprises in sequence, a promoter, a second nucleic acid operably linked to the promoter and encoding the exogenous protein, an IRES element, and a third nucleic acid operably linked to the IRES element and encoding a second fluorescent protein, wherein the first and second fluorescent proteins emit fluorescence at different wavelengths;

(b) isolating a recombinant virus generated from the co-transfected first insect host of step (a) that emits the second fluorescence;

(c) infecting a second insect host with the isolated recombinant virus of step (b); and (d) harvesting the exogenous protein from the infected second insect host of step (c).

According to preferred embodiments of the present disclosure, the first and second insect hosts are the same hosts.

According to one preferred embodiment of the present disclosure, the IRES element of the transfer vector is a portion of a *Rhopalosiphum padi* virus (RhPV) IRES sequence at least 90% identical to SEQ ID NO:12.

According to preferred embodiments of the present disclosure, the first and second insect hosts may be AcMNPV-permissive cells or insect larvae, BmNPV-permissive cells or insect larvae, as well as MaviMNPV-permissive cells or insect larvae. According to further examples, the AcMNPV-permissive cells may be any of Sf9, Sf21, or Hi-5 cells; and the AcMNPV-permissive insect larvae are *Trichoplusia ni* or *Spodoptera frugiperda*. In another example, the BmNPV-permissive cells are BmN cells; and the BmNPV-permissive insect larvae are *Bombyx mori*. In still another example, the MaviMNPV-permissive cells are NTU-MV532 cells; and the MaviMNPV-permissive insect larvae are *Maruca Vitrata.*

According to embodiments of the present disclosure, the exogenous protein may be any of an insect toxic protein, a therapeutic protein or a reporter protein. In one example, the exogenous protein is an insect toxic protein, preferably a protein toxic to *Lepidoptera.*

In some embodiments of the present disclosure, the first and second fluorescent proteins may be respectively selected from the group consisting of GFP, EGFP, DsRed, BFP, EYFP, amFP, zFP, dsFP, and cFP. In one preferred example, the first and second fluorescent proteins are EGFP and DsRed, respectively.

The details of one or more embodiments of the invention are set forth in the accompanying description below. Other features and advantages of the invention will be apparent from the detail descriptions, and from claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with reference to the following description, appended claims and the accompanying drawings, where:

DESCRIPTION

Figure 1:
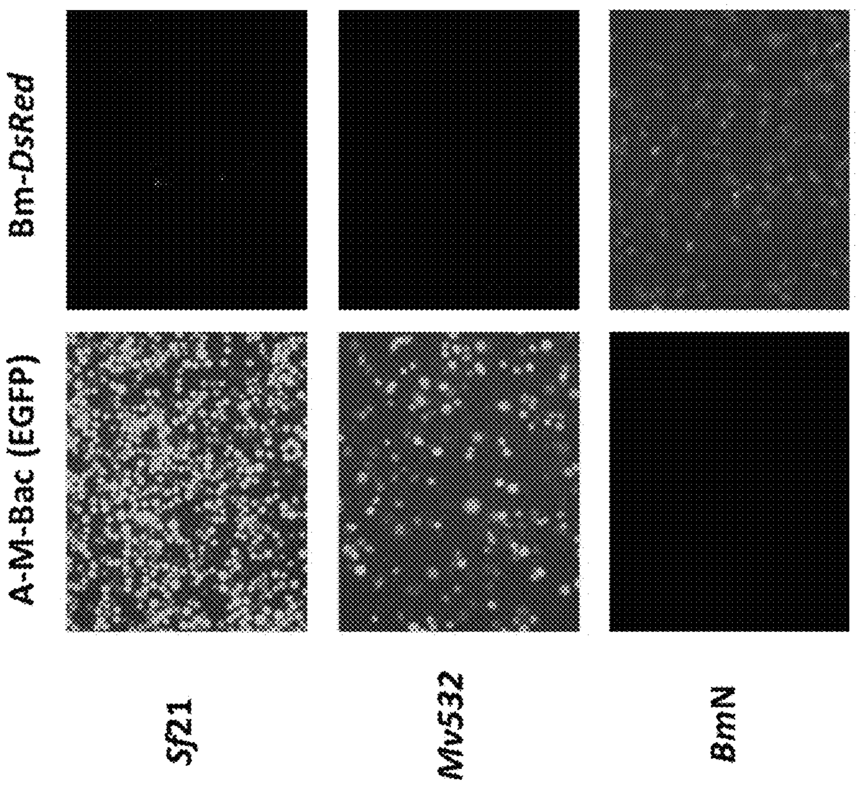
FIG. 1 are fluorescent photographs of Sf21 cells, NTU-MV532 cells, and BmN cells infected with the hybrid AcMv virus of example 1.2.1 (i.e., "A-M-Bac") or the Bm-DsRed of example 1.1.4, the photographs were respectively taken under FITC and rhodamine in accordance with example 1.2.2 of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

"Nucleotide sequence", "polynucleotide" or "nucleic acid" can be used interchangeably and are understood to mean, according to the present disclosure, either a double-stranded DNA, a single-stranded DNA or products of transcription of the said DNAs (e.g., RNA molecules). It should also be understood that the present disclosure does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The percentage of identity between a subject sequence and a reference standard can be determined by submitting both sequences to a computer analysis with any parameters affecting the outcome of the alignment set to the default position. Optimal alignment of sequences for aligning a comparison window are well known to those skilled in the art and may be conducted by tools such as the homology alignment algorithm, include, but are not limited to GAP, BESTFIT, FASTA, and TFASTA (Accelrys Inc., Burlington, Mass., USA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more nucleic acid sequences may be to a full-length nucleic acid sequence or a portion thereof, or to a longer nucleic acid sequence. In some instances, a subject sequence and the reference standard can exhibit the required percent identity without the introduction of gaps into one or both sequences. In many instances, the extent of identity will be evident without computer assistance The term "operably linked" refers to nucleotide sequences which are linked in the proper reading frame, whether to encode a mRNA transcript of a desired gene product or for a desired regulatory control. Operably linked can also mean that both the first and second nucleic acids are encoded by the same transcription unit. Translation of both such proteins can be regulated by various modes, including cap-dependent translation of the first open-reading-frame (ORF) located furthermost 5' on the transcription unit. Translation of the second ORF located downstream of the first ORF can be regulated by an IRES. Alternatively, both the first and second genes can be encoded by one ORF, yielding one contiguous polypeptide with both biological activities.

The term “toxic” as used herein means that the exogenous proteins produced by the method of the present disclosure with the aid of the identified AcMNPV based hybrid baculovirus are lethal to *Lepidoptera* insects.

The singular forms “a”, “an”, and “the” are used herein to include plural referents unless the context clearly dictates otherwise.

II. Description of the Invention

The practices of this invention are hereinafter described in detail with respect to a novel AcMNPV based hybrid baculovirus capable of infecting at least three different insect hosts. This novel AcMNPV based hybrid baculovirus are thus useful as a means for producing exogenous proteins, such as insect toxic proteins, in at least three different insect hosts, hence may act as an insecticide capable of reaching a wider range of hosts.

The first objective of the present disclosure is to provide an *Autographa californica* multiple nucleopolyhedrovirus (AcMNPV) based hybrid baculovirus. The AcMNPV based hybrid baculovirus is capable of infecting at least three different hosts and is characterized in having at least *Bombyx mori* nuclear polyhedrosis virus (BmNPV) genes of lef9, vlf1, p6.9, and vp80; *Maruca vitrata* multiple nucleopolyhedrovirus (MaviMNPV) genes of lef2, orf1629, and pe38; and AcMNPV/BmNPV/MaviMNPV-hybrid genes of pk1 (SEQ ID NO: 1), lef8 (SEQ ID NO: 2), DNA pol (SEQ ID NO: 3), GP41 (SEQ ID NO: 4), helicase (SEQ ID NO: 5), orf94 (SEQ ID NO: 6), VP1054 (SEQ ID NO: 7), orf65 (SEQ ID NO: 8), lef4 (SEQ ID NO: 9), lef5 (SEQ ID NO: 10), and orf99 (SEQ ID NO: 11).

To generate the AcMNPV based hybrid baculovirus of the present disclosure, with capability of infecting at least three types of insect hosts, a precursor virus was first made. This precursor virus is a hybrid virus of AcMNPV and MaviMNPV (herein after “AcMv”) and is capable of infecting at least two different hosts. The AcMv may be produced by the procedures described in a co-pending U.S. patent application Ser. No. 14/203,489 filed by Wu et al on Mar. 10, 2014, its entirety is herein incorporated by reference. Accordingly, the AcMNPV based hybrid baculovirus of the present disclosure is produced by co-infecting a first insect host, such as an AcMNPV-permissive insect cell line or larvae, a BmNPV-permissive cell line or larvae, or a MaviMNPV-permissive cell line or larvae, with the hybrid AcMv virus capable of expressing a first fluorescent protein, and a recombinant BmNPV virus capable of expressing a second fluorescent protein, in which the first and second fluorescent protein emit fluorescence at different wavelengths. In one preferred embodiment, the first host is an AcMNPV-permissive insect cell line Sf21.

Suitable fluorescent protein that may be used in the present disclosure includes, but is not limited to, green fluorescence protein (GFP), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), and *Clavularia* fluorescent protein (cFP). According to one preferred example, the hybrid AcMv virus and the recombinant BmNPV virus are engineered to express EGFP and DsRed, respectively. Accordingly, the first insect host of Sf21 cells successfully infected with the hybrid AcMv virus will emit green fluorescence due to the expression of EGFP, whereas those Sf21 cells infected with the recombinant BmNPV virus will not emit red fluorescence in the absence of the AcMv virus. If, however, the Sf21 cells were successfully co-infected with both viruses, then an emission of a yellow fluorescence is expected due to the expression of both EGFP and DsRed, in which DsRed might not be expressed if the cells were not infected with AcMv virus previously. Accordingly, Sf21 cells emitting yellow fluorescence are selected and the supernatant of these cells are collected and used to infect another batch of insect cells; the cultivation is monitored by the expression of fluorescent proteins until a single plaque is obtained.

To verify whether the virus collected from the single plaque contains hybrid genes, a second insect host, or a host differs from the previous host of Sf21 cells is subsequently infected with such virus. In one preferred example, the second insect host is BmNPV-permissive cells or larvae. Infection procedures are repeated again until another single viral plaque is obtained, and virus collected there from is subject to whole genome sequence analysis, which confirmed the identified hybrid virus is AcMNPV based hybrid baculovirus and comprises at least *Bombyx mori* nuclear polyhedrosis virus (BmNPV) genes of lef9, vlf1, p6.9, and vp80; *Maruca vitrata* multiple nucleopolyhedrovirus (MaviMNPV) genes of lef2, orf1629, and pe38; and AcMNPV/BmNPV/MaviMNPV-hybrid genes of pk1 (SEQ ID NO: 1), lef8 (SEQ ID NO: 2), DNA pol (SEQ ID NO: 3), GP41 (SEQ ID NO: 4), helicase (SEQ ID NO: 5), orf94 (SEQ ID NO: 6), VP1054 (SEQ ID NO: 7), orf65 (SEQ ID NO: 8), lef4 (SEQ ID NO: 9), lef5 (SEQ ID NO: 10), and orf199 (SEQ ID NO: 11).

Among the AcMNPV/BmNPV/MaviMNPV-hybrid genes, pk1 is derived from the hybrid of BmNPV and MaviMNPV; and lef8, DNA pol, GP41, helicase, orf94, VP1054, orf65, lef4, lef5, and orf99 are respectively derived from the hybrid of AcMNPV and BmNPV.

Further, the AcMNPV based hybrid baculovirus is characterized in containing the nucleic acid that encodes the first fluorescent protein originated from the hybrid AcMv virus in its genomic DNA. Suitable fluorescent protein includes, but is not limited to, GFP, EGFP, DsRed, BFP, EYFP, amFP, zFP, dsFP, and cFP. In the preferred example, the AcMNPV based hybrid baculovirus is characterized in containing the nucleic acid that encodes EGFP.

The thus produced AcMNPV based hybrid baculovirus is capable of infecting: (1) AcMNPV-permissive cells or insect larvae, (2) BmNPV-permissive cells or insect larvae, as well as (3) MaviMNPV-permissive cells or insect larvae. In some examples, the AcMNPV-permissive cells may be any of Sf9, Sf21, or Hi-5 cells; and the AcMNPV-permissive insect larvae are *Trichoplusia ni* or *Spodoptera frugiperda*. In another example, the BmNPV-permissive cells are BmN cells; and the BmNPV-permissive insect larvae are *Bombyx mori*. In still another example, the MaviMNPV-permissive cells are NTU-MV532 cells; and the MaviMNPV-permissive insect larvae are *Manuca Vitrata*.

Since the afore-identified AcMNPV based hybrid baculovirus is capable of infecting at least three different types of insect hosts, it is therefore a useful means for delivering foreign genes to different insect hosts. Accordingly, it is the second object of the present disclosure to provide a method of producing an exogenous protein in an insect host by use of the AcMNPV based hybrid baculovirus of the present disclosure.

In the present method, a first insect host, any of AcMNPV-permissive, BmNPV-permissive, or MaviMNPV-permissive cells or insect larvae are co-infected with the afore-identified AcMNPV based hybrid baculovirus genomic DNA of the present disclosure, which contains a first nucleic acid encoding a first fluorescence protein (e.g., EGFP), and a transfer vector. The transfer vector is constructed to comprise in sequence, a promoter, a second nucleic acid operably linked to the promoter and encodes the exogenous protein, an internal initiation of translation (IRES) element, and a third nucleic acid operably linked to the IRES element and encodes a second fluorescent protein; in which the first and second fluorescent proteins emit fluorescence at different wavelengths. The extent of transfection of the first insect host is monitored by the expression of the first and second fluorescent proteins respectively delivered by the AcMNPV based hybrid baculovirus of the present disclosure and the transfer vector. If homologous recombination occurred between the AcMNPV based hybrid baculovirus of the present disclosure and the transfer vector, the DNA segment comprising the first fluorescent protein in the AcMNPV based hybrid baculovirus of the present disclosure would be replaced by the DNA segment comprising the exogenous protein and the second fluorescent protein of the transfer vector; therefore, the generation of a recombinant virus is able to be isolated from the transfected first insect hosts by monitoring the expressed second fluorescent protein (such as DsRed) in the host. The isolated recombinant viruses are then used to infect a second insect host, so that the exogenous protein may be mass produced in the second insect host. In one example, the first and second insect hosts are the same; whereas in another example, the first and second insect hosts are different from each other.

Suitable promoter for use in the transfer vector is any of a polyhedrin (polh) promoter, a p10 promoter, a cytomegalovirus (CMV) promoter, a CAG promoter composed of chicken β-actin promoter and CMV enhancer, other baculovirus-derived promoters (such as an IE1 promoter, an IE2 promoter, a p6.9 promoter, a VP39 promoter, or *Bombyx mori*-derived actin promoter), and etc. In one example, the promoter is a polh promoter.

IRES sequences are distinct regions of RNA molecules that are able to attract the eukaryotic ribosome to the mRNA molecule and, therefore, allow translation initiation to occur. It is common that IRESes are located at the 5'-untranslated region (5'UTR) of some RNA viruses such as small RNA viruses or hepatitis C viruses and allow translation of the RNAs in a cap-independent manner. When an IRES element is placed between two open reading frames (ORFs) in an eukaryotic mRNA molecule, it can drive translation of the downstream protein coding region independently of the 5'-cap structure bound to the 5'-end of the mRNA molecule. In such setup, both proteins are produced in the host cell. Any known IRES sequence, either natural or chimeric, may be used to construct the transfer vector of in the present disclosure. According to preferred embodiments of the present disclosure, the IRES element of the transfer vector is a portion of a *Rhopalosiphum padi* virus (RhPV) IRES sequence at least 90% identical to SEQ ID NO: 12.

Exogenous proteins that may be expressed in the insect host using the AcMNPV based hybrid baculovirus of the present disclosure include at least, therapeutic proteins, insect toxic proteins or a combination thereof. Accordingly, depending on the desired exogenous proteins to be expressed, the AcMNPV based hybrid baculovirus of the present disclosure may turn the insect host into a bio-factory for mass production of therapeutic proteins, which include, but are not limited to, albumin, globulins (e.g., α-globuin), monoclonal antibodies, interferons, insulin, epidermal growth factor (EGF), erythropoietin, blood factors, and blood clotting factors. Alternatively, the AcMNPV based hybrid baculovirus of the present disclosure may carry genes of insect toxic proteins, preferably, proteins that are toxic to *Lepidoptera*, and act as a bio-insecticide that is effective to at least three different insect hosts. Examples of insect toxic proteins include, but are not limited to, ricin, cholera toxin, botulism toxin, scorpion neurotoxin or diphtheria toxin.

According to preferred embodiments of the present disclosure, the first and second insect hosts may be AcMNPV-permissive cells or insect larvae, BmNPV-permissive cells or insect larvae, as well as MaviMNPV-permissive cells or insect larvae. According to further examples, the AcMNPV-permissive cells may be any of Sf9, Sf21, or Hi-5 cells; and the AcMNPV-permissive insect larvae are *Trichoplusia ni* or *Spodoptera frugiperda*. In another example, the BmNPV-permissive cells are BmN cells; and the BmNPV-permissive insect larvae are *Bombyx mori*. In still another example, the MaviMNPV-permissive cells are NTU-MV532 cells; and the MaviMNPV-permissive insect larvae are *Maruca Vitrata*. In one preferred example, both the first and second insect hosts are Sf21 cells.

In some embodiments of the present disclosure, the first and second fluorescent proteins may be respectively selected from the group consisting of GFP, EGFP, DsRed, BFP, EYFP, amFP, zFP, dsFP, and cFP. In one preferred example, the first and second fluorescent proteins respectively conferred by the AcMNPV based hybrid baculovirus of the present disclosure and the transfer vector are EGFP and DsRed, respectively.

To provide those skilled in the art the tools to use the present disclosure, the AcMNPV based hybrid baculovirus and host cells of this invention may be assembled to kits. The components included in the kits are viral vector, enzymatic agents for making recombinant viral constructs, cells for amplification of the viruses, and reagents for transfection and transduction into the host cells, as well as description in a form of pamphlet, tape, CD, VCD or DVD on how to use the kits.

The following examples illustrate the construction and identification of the hybrid baculovirus of the present invention and the use thereof in the production of an exogenous protein in three different insect hosts. The examples are illustrative only, and do not limit the scope of the present invention.

Examples

Materials and Methods

Cell Culture

Sf21 cells, BmN cells, and NTU-MV532 cells, which derived from insect larvae of *Maruca Vitrata*, were cultured in TNM-FH medium containing 8-10% heat-inactivated fetal bovine serum (FBS) until a confluent cell monolayer was obtained.

Whole Genome Sequencing

The genome of the hybrid virus of the present disclosure was sequenced by Illumina MiSeq (Re-sequencing, 2×250 bp). The sequence was de novo assembled in accordance with procedures described by Zerbino D R et al ("Velvet: algorithms for de novo short read assembly using de Bruijn graphs." Genome research 2008, 18 (5): 821-829).

Western Blot Analysis

After the cells were infected with the recombinant viruses for 4 days, the proteins in the cell extracts were separated by SDS-PAGE according to the procedure of Laemmli on a mini Protein III system (Bio-Rad). The SDS-PAGE separated proteins were electro-transferred to a PVDF (polyvinyldiene difluoride) membrane (Millipore), which was then blocked with Tris-buffered saline (TTBS: 100 mM Tris, pH 7.4, 100 mM NaCl, and 0.1% Tween 20) containing 5% BSA (Sigma)

at room temperature for 1 h with gentle shaking on an orbital shaker. Subsequently, membranes were incubated overnight at 4° C. with PBS-diluted anti-HA antibody (1:1000) or anti-PCV2 antibody (1:2000). Unbound antibodies were removed by three 5-min washes in TTBS buffer at room temperature with shaking Membranes were then incubated with 1:2500 diluted alkaline phosphate (AP) secondary antibodies (Jackson) for 1 h at room temperature. The AP on the membrane was detected by an enhanced chemiluminescence kit (Pierce) following the protocol provided by the manufacturer.

Example 1

Generation and characterization of hybrid AcBmMv baculovirus 1.1 Plasmid Construction and Virus Generation 1.1.1 Construction and Generation of Egfp-Mavi The egfp-Maviwas constructed in accordance with procedures described by Chen Y R et al. ("Genomic and host range studies of *Maruca vitrata* nucleopolyhedrovirus." Journal of General Virology 2008, 89: 2315-2330).

1.1.2 Construction and Generation of Ac-DsRed

The DsRed gene (derived from plasmid pDsRed-N1, Clon-Tech, USA) was sub-cloned into the pBlubac4.5 transfer vector and the resulting plasmid was named pBacDsRed. The pBacDsRed (0.8 ug) was co-transfected with viral DNA Bac-N-Blue (0.2 ug, Invitrogen, USA) into Sf21 cells using Cellfectin (1 ul, Invitrogen, USA) and the resulting recombinant virus was purified by end point dilution and named Ac-DsRed.

1.1.3 Construction and Generation of Ac-Egfp

The egfp gene (derived from plasmid pEGFP-C1, Clon-Tech, USA) was sub-cloned into the pBlubac4.5 transfer vector and the resulting plasmid was named pBacEGFP. The pBacEGFP (0.8 ug) was co-transfected with viral DNA Bac-N-Blue (0.2 ug, Invitrogen, USA) into Sf21 cells using Cellfectin (1 ul, Invitrogen, USA) and the resulting recombinant virus was purified by end point dilution and named Ac-egfp.

1.1.4 Construction and Generation of Bm-DsRed

The Bm-DsRed was constructed in accordance with procedures described by Liao C H et al. ("Study on the Production of Foreign Proteins in Silkworm (*Bombyx mori* L.)" BULLETIN OF MIAOLIDISTRICT AGRICULTURALRESEARCH AND EXTENSIONSTATION 2011, 02:01-12).

1.1.5 Construction of pMv-L-HA-RP110-DsRed

The fragment of HA-RP110-DsRed was chemically synthesized and cloned into pUC18 cloning vector to generate the plasmid pUC18-HA-RP110-DsRed, in which the hemagglutinin (HA) gene was derived from avian influenza virus H5N2. The baculovirus transfer vector pMv-polh-total with XbaI and SacII was then digested and ligated with the HA-RP110-DsRed DNA fragment (derived from pUC18-HA-RP110-DsRed by restriction enzyme XbaI and SacII) by T4 DNA ligase and the resultant recombinant transfer plasmid was named pMv-L-HA-RP110-DsRed.

1.1.6 Construction of pMv-PCV2-RP110-DsRed

The fragment of PCV2-RP110-DsRed was chemically synthesized and cloned into pUC18 cloning vector to generate the plasmid pUC18-PCV2-RP110-DsRed, in which the PCV2-cap (PCV2) gene was derived from porcine circle virus type2. The baculovirus transfer vector pMv-polh-total with XhoI was then digested and ligated with the PCV2-RP110-DsRed DNA fragment (derived from pUC18-PCV2-RP110-DsRed by restriction enzyme XhoI and SalI) by T4 DNA ligase and the resultant recombinant transfer plasmid was named pMv-L-PCV2-RP110-DsRed.

1.2 Generation of Hybrid AcBmMv Baculovirus 1.2.1 Generation of Hybrid AcMv Baculovirus Sf21 cells were seeded at a density of $2\times10^5$ cells/well and cultivated in a media containing 10% FBS. Half an hour later, the cells were co-infected with the recombinant egfp-Mavi virus of example 1.1.1 and the recombinant Ac-DsRed virus of example 1.1.2 at the multiplicity of infection (moi) of 1 and 10, respectively. 1.5 to 2 hours after the infection, the media were replaced by fresh culture media supplemented with 10% FBS, and the cells were incubated at 27° C. for 5 days to allow the recombination of egfp-Mavi virus and Ac-DsRed virus. The cells successfully infected with recombinant egfp-Mavi virus of example 1.1.1 emitted green fluorescence (view under FITC filter), whereas cells successfully infected with Ac-DsRed virus of example 1.1.2 emitted red fluorescence (view under rhodamine filter). It was noted that some cells exhibited yellow fluorescence, indicating the cells were co-infected with the two viruses, in which both EGFP and DsRed were expressed that give rise to the merged yellow fluorescence. The culture medium of the co-infected cells that emitted yellow fluorescence was then collected and used to infect another batch of Sf21 cells.

Five days post-infection, the culture medium was again collected and used to infect MaviMNPV-permissive cells (i.e., NTU-MV532 cells). And then, this culture medium was collected and used to conduct the end point dilution in NTU-MV532 cells to isolate the single viral clones. A desired hybrid AcMv virus was eventually selected from the single viral plaque.

1.2.2 Generation of Hybrid AcBmMv Baculovirus

Sf21 cells were seeded at a density of $2\times10^5$ cells/well and cultivated in a media containing 10% FBS. Half an hour later, the cells were co-infected with the hybrid AcMv virus of example 1.2.1 and the recombinant Bm-DsRed virus of example 1.1.4 at the moi of 1 and 10, respectively. 1.5 to 2 hours after the infection, the media were replaced by fresh culture media supplemented with 10% FBS, and the cells were incubated at 27° C. for 5 days to allow the recombination of hybrid AcMv virus and Bm-DsRed virus. As depicted in FIG. 1, cells successfully infected with the hybrid AcMv virus of example 1.2.1 (or"A-M-Bac") emitted green fluorescence (view under FITC filter), whereas cells successfully infected with Bm-DsRed virus of example 1.1.4 emitted red fluorescence (view under rhodamine filter). It was noted that some cells exhibited yellow fluorescence, indicating that cells were co-infected with two different viruses, in which both EGFP and DsRed were expressed that give rise to the merged yellow fluorescence (data not shown). The culture medium of the co-infected cells that emitted yellow fluorescence was then collected and used to infect another batch of Sf21 cells.

Five days post-infection, the culture medium was again collected and used to infect BmNPV-permissive cells (i.e., BmN cells). Subsequently, the culture medium was collected again and used to conduct end point dilution in BmN cells to isolate the single viral clones. A desired hybrid AcBmMv virus was eventually selected from the single viral plaque.

Example 2

Characterization of the Hybrid AcBmMv Baculovirus of Example 1.2.2

The selected desired hybrid AcBmMvvirus of Example 1.2.2 was subject to further analysis including cross host infection analysis and whole genome sequencing.

2.1 Cross Host Infection Analysis

To test whether the selected hybridAcBmMv virus of Example 1.2.2 does possess cross host infection capability, AcMNPV-permissive cells (e.g., Sf21 or Hi-5 cells), MaviMNPV-permissive cells (e.g., NTU-MV532 cells), and BmNPV-permissive cells (e.g., BmN cells) were infected with the selected hybrid AcBmMv virus of Example 1.2.2, and the infection was monitored by the measurement of green fluorescence emitted by the expressed EGFP or red fluorescence emitted by the expressed DsRed. Results are illustrated in FIG. 2.

Figure 2:
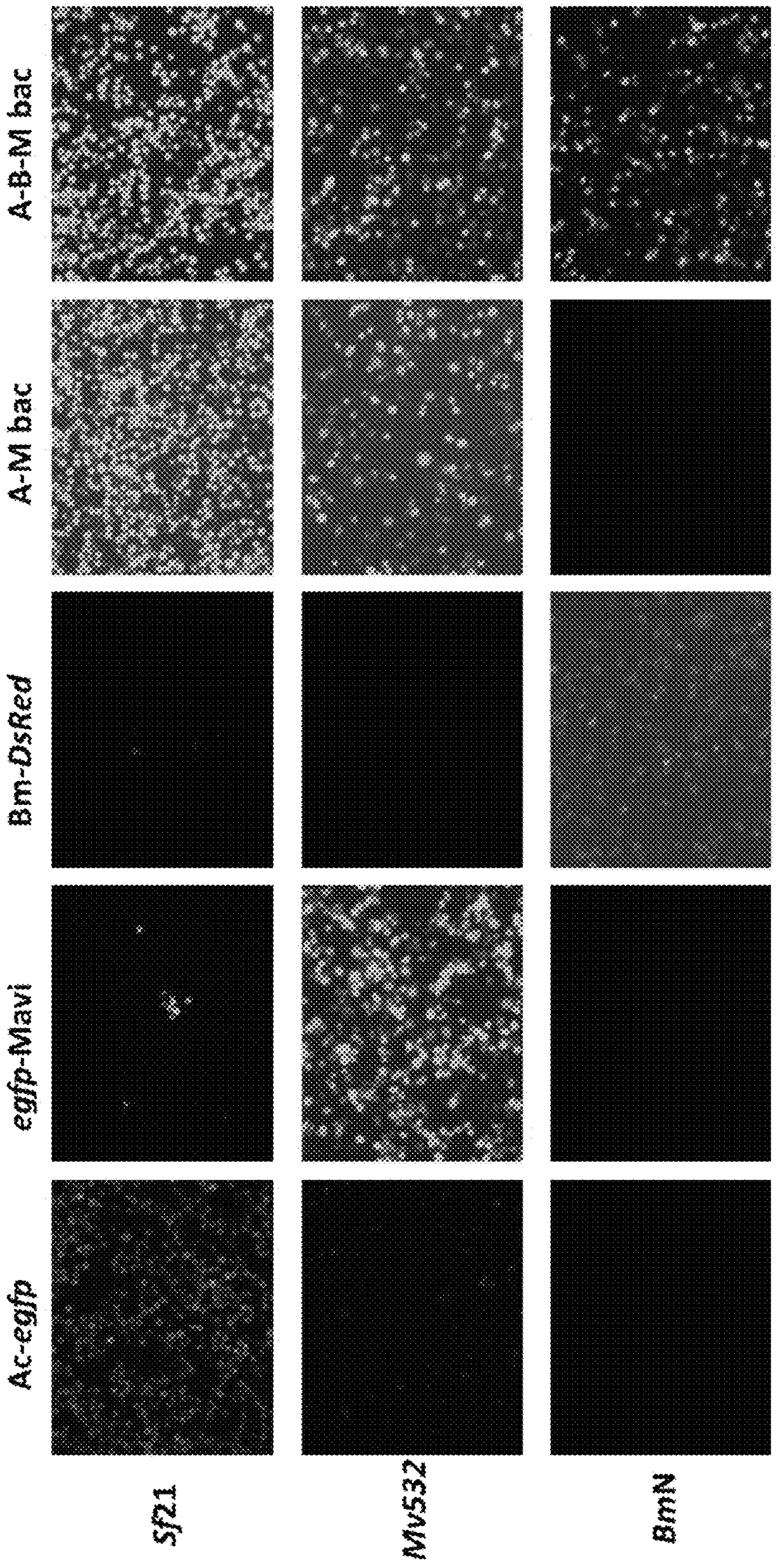
FIG. 2 are photographs of Sf21 cells, NTU-MV532 cells, and BmN cells, respectively, infected with Ac-egfp of example 1.1.3, egfp-Mavi of example 1.1.1, Bm-DsRed of example 1.1.4, the hybrid AcMv virus of example 1.2.1 and the hybrid AcBmMv virus of example 1.2.2 in according to example 2.1 of the present disclosure.

For Sf21 cells, which are permissive to AcMNPV and non-permissive to MaviMNPV and/or BmNPV, hence only cells infected with AcMNPV (i.e., Ac-egfp), hybrid AcMv virus, and/or hybrid AcBmMv virus were capable of emitting green fluorescence, whereas no fluorescence was observed for cells infected with MaviMNPV (i.e., egfp-Mavi) and/or BmNPV (i.e., Bm-DsRed) (upper panel, FIG. 2). Similar results were also observed in NTU-MV532 cells, which are permissive to MaviMNPV and non-permissive to AcMNPV and/or BmNPV. As illustrated in middle panel of FIG. 2, only cells infected with egfp-Mavi, hybrid AcMv virus, and hybrid AcBmMv virus were capable of emitting green fluorescence, whereas no fluorescence was observed in Ac-egfp and/or Bm-DsRed infected cells. Based on the same concept, BmN cells, permissive to BmNPV and non-permissive to AcMNPV and/or MaviMNPV, can only be infected with Bm-DsRed and/or hybrid AcBmMv virus and thus produced red fluorescence or green fluorescence, respectively; whereas cells infected by Ac-egfp, egfp-Mavi and/or hybrid AcMv virus would not generate any green fluorescence (lower panels, FIG. 2).

Thus, results in FIG. 2 indicate that the hybrid AcBmMv virus of Example 1.2.2 does possess cross host infection capability.

2.2 Whole Genome Sequencing

To identify the genes responsible for the cross host infection capability of the hybrid AcBmMv virus of Example 1.2.2, the virus was subject to whole genome sequencing, and sequence identity of each gene was then compared with corresponding AcMNPV, BmNPV, and MaviMNPV genes. The results are summarized in Table 1.

As evidenced from Table 1, the hybrid AcBmMv virus of Example 1.2.2 obviously possessed a backbone of AcMNPV, with 68% of genes identical to those of AcMNPV. ORFs derived from BmNPV included, orf35, orf36, odv-e66, ets, orf45, orf46, orf47, orf48, fp, lef9, orf51, gp37, orf61, orf62, vlf1, orf64, orf65, p6.9, orf87, vp80, he65, and orf90. ORFs derived from MaviMNPV included, orf1629, pe38, CDS57, ptp, CDS58, CDS59, and lef2. In addition, some hybrid ORFs were generated as well, which included pk1, orf4, orf36, orf41, orf46, orf47, DNA-pol, orf65, orf71, lef4, helicase, lef5, p40, orf94, orf99, and orf144.

TABLE 1

Comparison of homologous of ORFs among hybrid AcBmMv virus of example 1.2.2, AcMNPV, BmNPV, and MaviMNPV

| | | HOMOLOGOUS (% SIMILARITY) | | |
|---|---|---|---|---|
| NO. | NAME | AcMNPV | BmNPV | MaviMNPV |
| 1 | Mv_EGFP | — | — | — |
| 2 | Mv_ORF1629 | Ac9 (81.9) | Bm2 (80.0) | Mv2 (99.8) |
| 3 | ABM_pk1 | Ac10 (90.2) | Bm3 (89.9) | Mv3 (94.7) |
| 4 | ABM_Orf4 | Ac11 (97.9) | Bm4 (97.9) | Mv4 (84.7) |
| 5 | Ac_Orf12 | Ac12 (100) | — | — |

TABLE 1-continued

Comparison of homologous of ORFs among hybrid AcBmMv virus of example 1.2.2, AcMNPV, BmNPV, and MaviMNPV

| | | HOMOLOGOUS (% SIMILARITY) | | |
|---|---|---|---|---|
| NO. | NAME | AcMNPV | BmNPV | MaviMNPV |
| 6 | Ac_Orf13 | Ac13 (99.6) | Bm5 (95.0) | Mv5 (86.4) |
| 7 | Ac_lef1 | Ac14 (99.8) | Bm6 (95.8) | Mv6 (86.4) |
| 8 | Ac_egt | Ac15 (99.7) | Bm7 (95.5) | Mv7 (84.0) |
| 9 | Ac_Orf16 | Ac16 (99.9) | Bm9 (94.2) | Mv8 (69.8) |
| 10 | Ac_Orf17 | Ac17 (97.2) | Bm10 (95.8) | Mv9 (61.4) |
| 11 | Ac_Orf18 | Ac18 (99.7) | Bm11 (94.8) | Mv10 (87.5) |
| 12 | Ac_Orf19 | Ac19 (98.2) | Bm12 (94.0) | Mv11 (88.2) |
| 13 | Ac_Orf20 | Ac20 (91.0) | — | — |
| 14 | Ac_Orf21 | Ac21 (99.5) | Bm13 (88.2) | Mv12 (59.7) |
| 15 | Ac_Orf22 | Ac22 (99.3) | Bm14 (94.5) | Mv13 (88.6) |
| 16 | Ac_env-prot | Ac23 (99.6) | Bm15 (92.7) | Mv14 (75.4) |
| 17 | Ac_pkip | Ac24 (100) | Bm16 (93.9) | Mv15 (83.0) |
| 18 | Ac_Orf25 | Ac25 (99.0) | Bm17 (95.7) | Mv16 (85.9) |
| 19 | Ac_Orf26 | Ac26 (99.7) | Bm18 (94.4) | Mv17 (83.3) |
| 20 | Ac_IAP1 | Ac27 (99.4) | Bm19 (93.6) | Mv18 (75.6) |
| 21 | Ac_lef6 | Ac28 (100) | Bm20 (94.6) | Mv19 (47.1) |
| 22 | Ac_Orf29 | Ac29 (99.5) | — | — |
| 23 | Ac_Orf30 | Ac30 (99.9) | Bm21 (94.6) | Mv21 (82.0) |
| 24 | Ac_Orf31 | Ac31 (100) | Bm25 (97.1) | Mv22 (81.9) |
| | | Hr2 | | |
| 25 | Ac_fgf | Ac32 (100) | Bm26 (94.5) | — |
| 26 | Ac_HisP | Ac33 (100) | — | — |
| 27 | Ac_Orf34 | Ac34 (99.7) | Bm27 (93.2) | Mv23 (79.1) |
| 28 | Ac_v-ubi | Ac35 (99.6) | Bm28 (98.3) | Mv24 (91.0) |
| 29 | Ac_39K/pp31 | Ac36 (99.6) | Bm29 (93.9) | Mv25 (81.5) |
| 30 | Ac_lef11 | Ac37 (100) | Bm30 (96.2) | Mv26 (84.2) |
| 31 | Ac_Orf38 | Ac38 (100) | Bm31 (95.7) | Mv27 (84.5) |
| 32 | Ac_p43 | Ac39 (99.4) | Bm32 (95.8) | Mv28 (80.7) |
| 33 | Ac_p47 | Ac40 (97.8) | Bm33 (96.7) | Mv29 (89.6) |
| 34 | Ac_Orf41 | Ac41 (100) | Bm34 (89.1) | Mv30 (84.4) |
| 35 | Ac_GTA | Ac42 (99.7) | Bm35 (96.4) | — |
| 36 | ABM_Orf36 | Ac43 (93.7) | Bm36 (97.9) | Mv31 (75.2) |
| 37 | Bm_Orf35 | Ac44 (96.2) | Bm37 (99.7) | Mv32 (74.5) |
| 38 | Bm_Orf36 | Ac45 (93.0) | Bm38 (98.5) | Mv33 (81.1) |
| 39 | Bm_odv-e66 | Ac46 (95.9) | Bm39 (96.9) | — |
| 40 | Bm-ets | Ac47 (93.3) | Bm40 (99.3) | Mv34 (81.0) |
| 41 | ABM_Orf41 | Ac50 (99.2) | Bm41 (97.4) | Mv35 (89.6) |
| 42 | Ac_Orf51 | Ac51 (99.8) | Bm42 (96.1) | Mv36 (88.2) |
| 43 | Ac_Orf52 | Ac52 (99.7) | Bm43 (95.9) | Mv37 (86.3) |
| 44 | Ac_Orf53 | Ac53 (99.8) | Bm44 (96.4) | Mv38 (87.9) |
| 45 | Ac_lef10 | Ac53a (99.6) | Bm45 (98.3) | Mv39 (90.7) |
| 46 | ABM_Orf46 | Ac54 (97.5) | Bm46 (98.5) | Mv40 (88.5) |
| 47 | ABM_Orf47 | Ac55 (96.4) | Bm47 (94.0) | Mv41 (79.3) |
| 48 | Bm_Orf45 | Ac56 (93.3) | Bm48 (98.8) | Mv42 (80.8) |
| 49 | Bm_Orf46 | Ac57 (96.3) | Bm49 (99.8) | — |
| 50 | Bm_Orf47 | Ac58 + 59 (89.2) | Bm50 (100) | Mv43 (78.3) |
| 51 | Bm_Orf48 | Ac60 (86.0) | Bm51 (98.0) | Mv44 (86.4) |
| 52 | Bm_fp | Ac61 (97.8) | Bm52 (99.2) | Mv45 (87.3) |
| 53 | Bm_lef9 | Ac62 (95.3) | Bm53 (97.6) | Mv46 (89.7) |
| 54 | Bm_Orf51 | Ac63 (94.4) | Bm54 (98.9) | Mv47 (83.8) |
| 55 | Bm_gp37 | Ac64 (94.6) | Bm55 (99.1) | Mv48 (86.3) |
| 56 | ABM_DNA-pol | Ac65 (97.9) | Bm56 (96.9) | Mv49 (88.9) |
| 57 | Ac_Orf66 | Ac66 (100) | Bm57 (95.0) | Mv50 (82.3) |
| 58 | Ac_lef-3 | Ac67 (99.6) | Bm58 (94.1) | Mv51 (83.7) |
| 59 | Ac_Orf68 | Ac68 (99.7) | Bm59 (93.1) | Mv52 (86.1) |
| 60 | Ac_Orf69 | Ac69 (99.9) | Bm60 (87.6) | Mv53 (77.1) |
| 61 | Ac_Orf70 | Ac70 (99.9) | — | — |
| 62 | Ac_IAP2 | Ac71 (99.1) | Bm61 (95.3) | Mv54 (83.7) |
| 63 | Ac_Orf72 | Ac72 (100) | Bm62 (88.0) | Mv55 (78.7) |
| 64 | Ac_Orf73 | Ac73 (100) | Bm63 (93.7) | Mv56 (86.0) |
| 65 | ABM_Orf65 | Ac74 (95.2) | Bm64 (98.6) | Mv57 (82.8) |
| 66 | Bm_Orf61 | Ac75 (94.5) | Bm65 (97.5) | Mv58 (85.6) |
| 67 | Bm_Orf62 | Ac76 (95.7) | Bm66 (100) | Mv59 (86.8) |
| 68 | Bm_vlf1 | Ac77 (91.2) | Bm67 (99.2) | Mv60 (84.9) |
| 69 | Bm_Orf64 | Ac78 (94.6) | Bm68 (99.1) | Mv61 (84.5) |
| 70 | Bm_Orf65 | Ac79 (97.8) | Bm69 (99.0) | Mv62 (89.2) |
| 71 | ABM_Orf71 | Ac80 (98.5) | Bm70 (94.7) | Mv63 (90.0) |
| 72 | Ac_Orf81 | Ac81 (100) | Bm71 (93.6) | Mv64 (88.2) |

TABLE 1-continued

Comparison of homologous of ORFs among hybrid AcBmMv virus of example 1.2.2, AcMNPV, BmNPV, and MaviMNPV

| | | HOMOLOGOUS (% SIMILARITY) | | |
|---|---|---|---|---|
| NO. | NAME | AcMNPV | BmNPV | MaviMNPV |
| 73 | Ac_TLP | Ac82 (99.8) | Bm72 (93.0) | Mv65 (85.3) |
| 74 | Ac_p95 | Ac83 (99.9) | Bm73 (94.7) | Mv66 (86.2) |
| | | Hr3 | | |
| 75 | Ac_Orf84 | Ac84 (99.6) | — | — |
| 76 | Ac_Orf85 | Ac85 (98.8) | — | — |
| 77 | Ac_PNK/PNL | Ac86 (99.8) | — | — |
| 78 | Ac_p15 | Ac87 (100) | Bm74 (95.5) | — |
| 79 | Ac_cg30 | Ac88 (99.9) | Bm75 (93.3) | — |
| 80 | Ac_vp39 | Ac89 (99.7) | Bm76 (94.8) | Mv67 (85.4) |
| 81 | ABM_lef4 | Ac90 (97.5) | Bm77 (99.1) | Mv68 (87.7) |
| 82 | Ac_Orf91 | Ac91 (96.3) | Bm78 (53.4) | — |
| 83 | Sequence from Sf21 Genomic DNA | — | — | — |
| 84 | Ac_Orf92 | Ac92 (100) | Bm79 (95.8) | Mv69 (91.0) |
| 85 | Ac_Orf93 | Ac93 (100) | Bm80 (98.1) | Mv70 (86.5) |
| 86 | Ac_odv-e25 | Ac94 (99.9) | Bm81 (93.0) | Mv71 (78.7) |
| 87 | ABM_helicase | Ac95 (97.1) | Bm82 (98.4) | Mv72 (83.4) |
| 88 | Ac_Orf96 | Ac96 (100) | Bm83 (89.4) | Mv73 (84.6) |
| 89 | Ac_Orf97 | Ac97 (100) | — | — |
| 90 | Ac_Orf98 | Ac98 (100) | Bm86 (90.1) | Mv75 (80.2) |
| 91 | ABM_lef5 | Ac99 (97.2) | Bm87 (98.7) | Mv76 (90.2) |
| 92 | Bm_p6.9 | Ac100 (82.1) | Bm88 (99.5) | Mv77 (64.5) |
| 93 | ABM_p40 | Ac101 (98.5) | Bm89 (98.3) | Mv78 (88.6) |
| 94 | ABM_Orf94 | Ac102 (98.4) | Bm90 (95.7) | Mv79 (81.9) |
| 95 | Bm_Orf87 | Ac103 (96.6) | Bm91 (99.8) | Mv80 (89.0) |
| 96 | Bm_vp80 | Ac104 (96.4) | Bm92 (99.9) | Mv81 (87.5) |
| 97 | Bm_he65 | Ac105 (49.5) | Bm93 (97.8) | Mv82 (85.3) |
| 98 | Bm_Orf90 | Ac106 (24.3) | Bm94 (98.3) | Mv83 (86.5) |
| 99 | ABM_Orf99 | Ac108 (97.5) | Bm95 (96.9) | Mv84 (88.4) |
| 100 | Ac_Orf109 | Ac109 (99.7) | Bm96 (96.2) | Mv85 (89.2) |
| 101 | Ac_Orf110 | Ac110 (100) | Bm97 (89.4) | Mv86 (93.6) |
| 102 | Ac_Orf111 | Ac111 (100) | Bm98 (93.1) | Mv87 (75.8) |
| 103 | Ac_Orf112 | Ac112 (98.1) | — | — |
| 104 | Ac_Orf113 | Ac113 (100) | — | — |
| | | Hr4b | | |
| 105 | Ac_Orf114 | Ac114 (99.9) | Bm99 (96.3) | Mv88 (85.3) |
| 106 | Ac_Orf115 | Ac115 (100) | Bm100 (95.0) | Mv89 (89.3) |
| 107 | Ac_Orf116 | Ac116 (100) | Bm101 (92.4) | — |
| 108 | Ac_Orf117 | Ac117 (100) | Bm102 (90.6) | Mv90 (84.0) |
| 109 | Ac_Orf118 | Ac118 (100) | — | — |
| 110 | Ac_Orf119 | Ac119 (99.5) | Bm103 (91.9) | Mv91 (86.2) |
| 111 | Ac_Orf120 | Ac120 (99.2) | Bm104 (95.2) | Mv92 (84.3) |
| | | Hr4c | | |
| 112 | Ac_Orf121 | Ac121 (100) | Bm105 (93.7) | — |
| 113 | Ac_Orf122 | Ac122 (100) | Bm106 (94.2) | — |
| 114 | Ac_pk2 | Ac123 (99.7) | Bm107 (96.2) | — |
| 115 | Ac-Orf124 | Ac124 (99.5) | Bm108 (93.0) | Mv93 (84.3) |
| 116 | Ac_lef7 | Ac125 (100) | Bm109 (88.2) | Mv94 (75.0) |
| 117 | Ac-chitinase | Ac126 (99.8) | Bm110 (95.7) | Mv95 (87.7) |
| 118 | Ac_v-cath | Ac127 (100) | Bm111 (96.6) | Mv96 (87.8) |
| 119 | Ac_gp64 | Ac128 (100) | Bm112 (95.1) | Mv97 (85.7) |
| 120 | Ac_p24 | Ac129 (100) | Bm113 (94.1) | Mv98 (84.4) |
| 121 | Ac_gp16 | Ac130 (100) | Bm114 (98.4) | Mv99 (83.2) |
| 122 | Ac_PE/pp34 | Ac131 (99.9) | Bm115 (70.6) | Mv100 (83.6) |
| 123 | Ac_Orf132 | Ac132 (99.5) | Bm116 (95.6) | Mv101 (83.9) |
| 124 | Ac_alk-exo | Ac133 (99.8) | Bm117 (96.2) | Mv102 (89.2) |
| 125 | Ac_94K | Ac134 (99.7) | Bm118 (83.3) | — |
| 126 | Ac_35K/p35 | Ac135 (100) | Bm120 (95.8) | Mv103 (84.6) |
| | | Hr5 | | |
| 127 | Ac_p26 | Ac136 (99.9) | Bm121 (94.6) | Mv104 (82.2) |
| 128 | Ac_p10 | Ac137 (99.6) | Bm122 (92.5) | Mv105 (61.1) |
| 129 | Ac-p74 | Ac138 (99.6) | Bm123 (94.7) | Mv106 (87.6) |
| 130 | Ac_ME53 | Ac139 (99.7) | Bm124 (92.6) | Mv107 (76.9) |
| 131 | Ac_Orf140 | Ac140 (98.4) | — | Ac108 (31.9) |
| 132 | Ac IE01 | Ac141a (99.9) | — | — |
| 133 | Ac_IE0 | Ac141 (99.7) | Bm125 (97.2) | Mv109 (81.1) |
| 134 | Ac_49K | Ac142 (99.9) | Bm126 (97.1) | Mv110 (87.0) |

TABLE 1-continued

Comparison of homologous of ORFs among hybrid AcBmMv virus of example 1.2.2, AcMNPV, BmNPV, and MaviMNPV

| | | HOMOLOGOUS (% SIMILARITY) | | |
|---|---|---|---|---|
| NO. | NAME | AcMNPV | BmNPV | MaviMNPV |
| 135 | Ac_odv-e18 | Ac143 (100) | Bm127 (82.5) | Mv111 (82.5) |
| 136 | Ac_odv-e27 | Ac144 (99.9) | Bm128 (92.7) | Mv112 (91.6) |
| 137 | Ac Orf145 | Ac145 (100) | Bm129 (76.4) | Mv113 (85.1) |
| 138 | Ac_Orf146 | Ac146 (100) | Bm130 (96.2) | Mv114 (87.2) |
| 139 | Ac_IE1 | Ac147 (99.9) | Bm131 (95.0) | Mv115 (85.9) |
| 140 | Ac_odv-e56 | Ac148 (99.9) | Bm132 (88.7) | Mv116 (68.8) |
| 141 | Ac_Orf149 | Ac149 (100) | Bm133 (90.3) | Mv117 (49.7) |
| 142 | Ac_Orf150 | Ac150 (100) | Bm134 (76.1) | Mv118 (43.1) |
| 143 | Ac_IE2 | Ac144 (99.9) | Bm128 (92.7) | Mv112 (91.6) |
| 144 | ABM_Orf144 | Ac152 (94.6) | — | Mv120 (61.8) |
| 145 | Mv_PE38 | Ac153 (62.9) | Bm136 (62.6) | Mv121 (99.9) |
| 146 | Mv_CDS57 | Ac154 (71.5) | Bm137 (71.4) | Mv122 (100) |
| | | Hr1 | | |
| 147 | Mv_ptp | Ac1 (80.8) | Bm138 (80.2) | Mv123 (99.8) |
| 148 | Mv_CDS58 | Ac4 (25.4) | Bm141 (25.2) | Mv124 (100) |
| 149 | Mv_CDS59 | Ac5 (75.7) | Bm142 (72.2) | Mv125 (100) |
| 150 | Mv_lef2 | Ac6 (84.1) | Bm143 (82.0) | Mv126 (100) |

Example 3

Production of Exogenous Protein by the Hybrid AcBmMv Baculovirus of Example 1.2.2

Figures 3A, 3B:
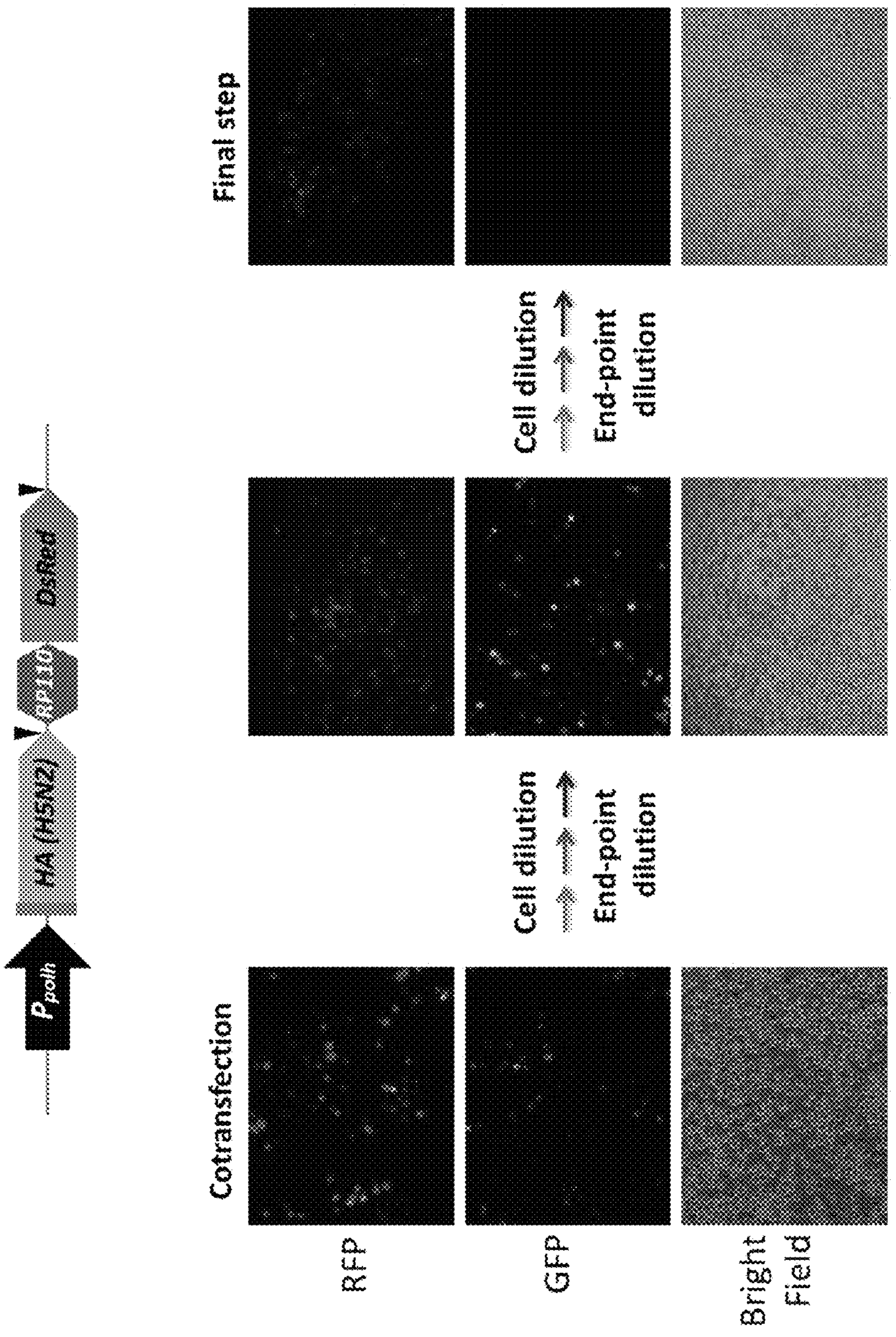
FIG. 3A is a schematic diagram of the HA containing-transfer vector constructed in according to example 1.1.5 of the present disclosure.
FIG. 3B are photographs of Sf21 cells infected with recombinant virus derived from a single plaque, the photographs were taken under FITC and rhodamine in accordance with example 3 of the present disclosure.

In this example, to verify whether the hybrid AcBmMv baculovirus of example 1.2.2 could produce exogenous proteins in three different host cells, (i.e., AcMNPV-permissive cells, BmNPV-permissive cells, and MaviMNPV-permissive cells), HA or PCV2-cap was used as an exemplified exogenous protein, and a transfer vector containing HA or PCV2-cap was constructed in according to procedures described in example 1.1.5 (i.e., pMv-L-HA-RP110-DsRed) or example 1.1.6 (i.e., pMv-PCV2-RP110-DsRed). FIG. 3A is a representative schematic diagram of the transfer vector containing HA. A transfer vector containing PCV2-cap gene may be constructed in a similar manner (not illustrated). The transfer vector was then used with the viral DNA of hybrid AcBmMv baculovirus of example 1.2.2 to co-transfect Sf21 cells, and a single hybrid virus strain containing HA was eventually selected by the red fluorescence under fluorescent microscope (FIG. 3B). The selected hybrid virus strain was then used to infect the host cells (i.e., Sf21 cells, BmN cells, and NTU-MV532 cells) and the infected host cells were subsequently cultivated at 27° C. for 3-4 days to allow the expression of HA protein. HA protein harvested from the infected host cells were analyzed by coomassie blue staining and further confirmed by western blot analysis.

Figure 4A:
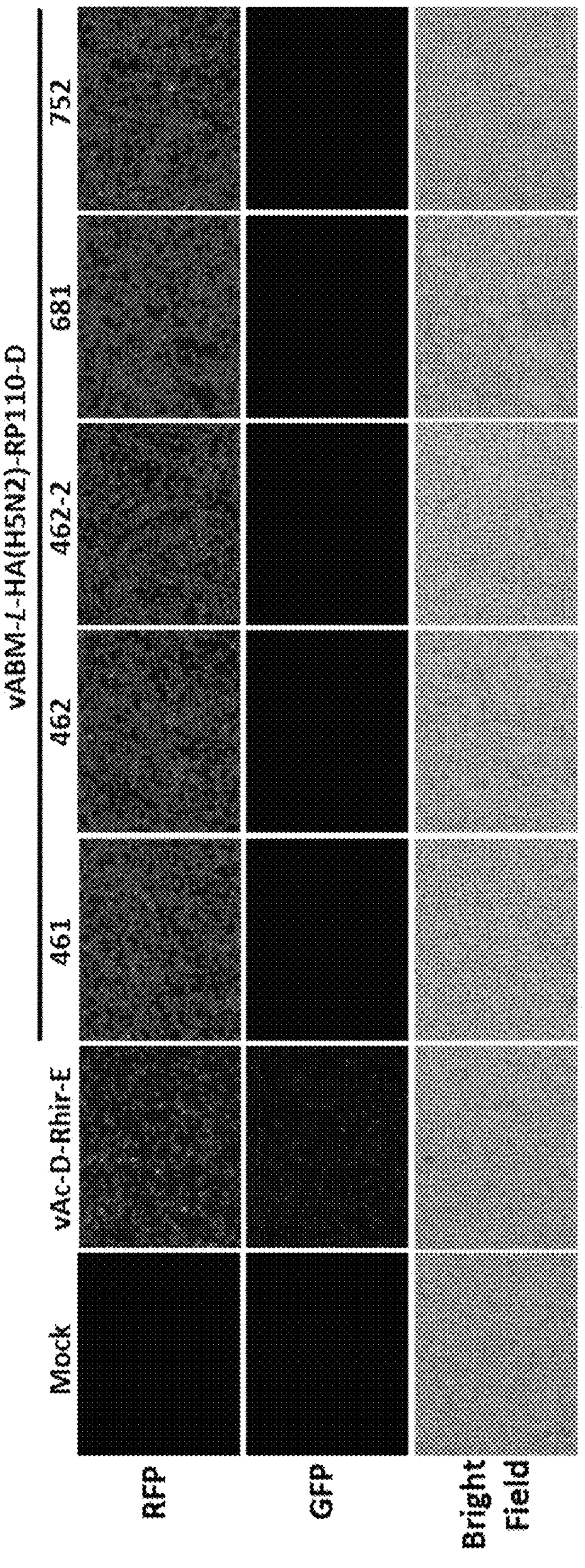
FIG. 4A are photographs of Sf21 cells infected with various isolated recombinant viruses, the photographs were taken under FITC and rhodamine in accordance with example 3 of the present disclosure.
Figure 4B:
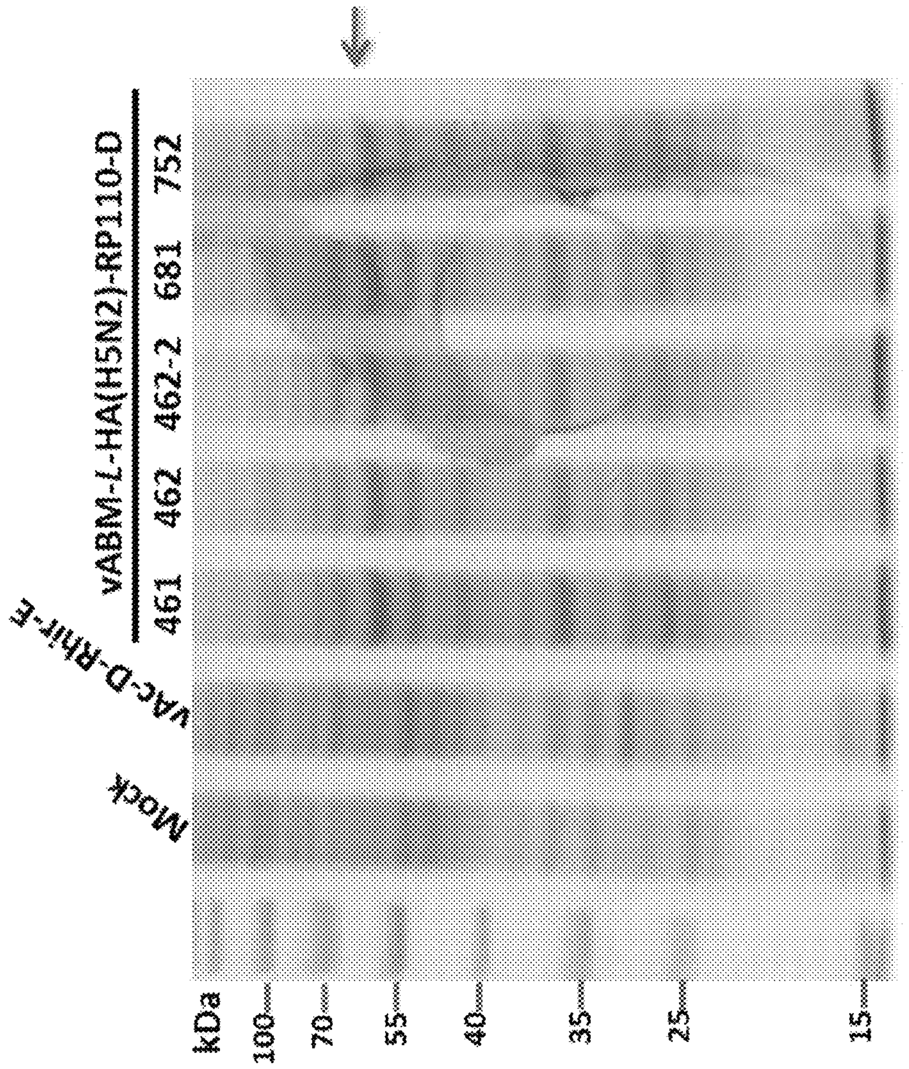
FIG. 4B is the coomassie staining analysis of protein extracted from Sf21 cells, which were infected with various isolated recombinant viruses in accordance with example 3 of the present disclosure, in which the HA protein band is indicated by the arrow.
Figure 4C:
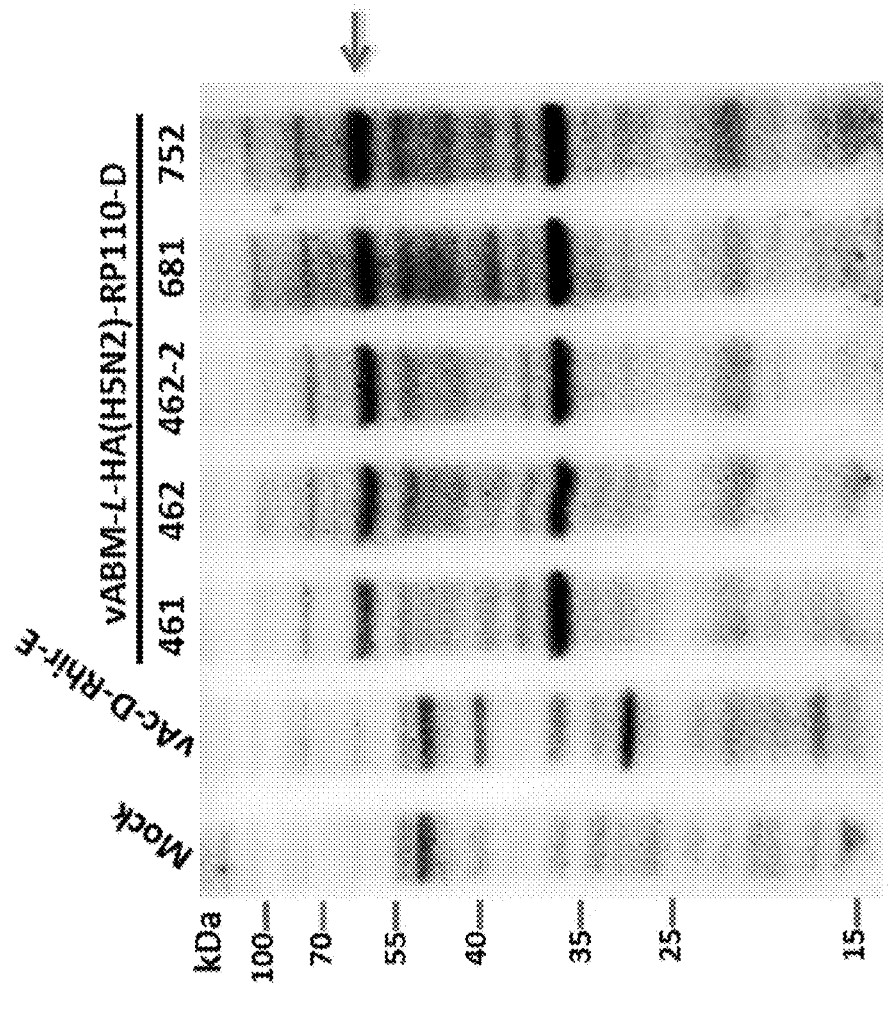
FIG. 4C is the western blot analysis of protein extracted from Sf21 cells infected with various isolated recombinant viruses in accordance with example 3 of the present disclosure, in which the HA protein band is indicated by the arrow.

FIG. 4A are fluorescent photographs of Sf21 cells infected with the recombinant virus containing HA gene (shown as vABM-L-HA-RP110-D) and the AcMNPV virus (shown as vAc-D-Rhir-E) served as a viral infection control. The data indicates that despite various isolated recombinant viruses were employed, they all produced similar infectious efficiency. The expression of the exogenous protein (e.g., HA protein) was also analyzed by coomassie blue staining (FIG. 4B) and further confirmed by western blot analysis using anti-HA antibody (FIG. 4C). With similar results, all Sf21 cells infected with different isolated recombinant viruses all expressed HA protein (approximately 65 kDa, indicated by arrows). It is noted that the expression levels of HA among various isolated recombinant viruses are relatively the same, which indicates that the recombinant virus of the present disclosure may serve as an expression vehicle to express the exogenous interesting gene in various hosts.

Figure 5A:
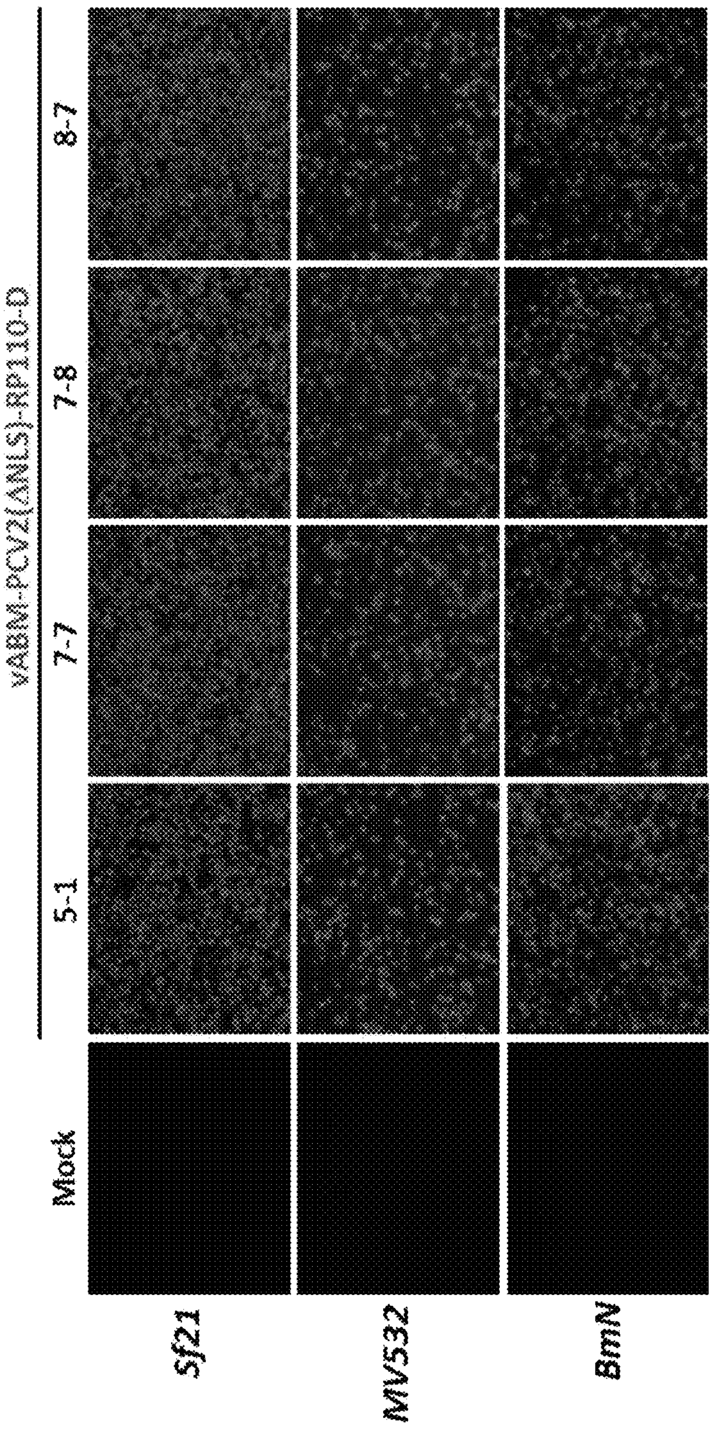
FIG. 5A are photographs of Sf21 cells, NTU-MV532 cells, and BmN cells respectively infected with various isolated recombinant viruses respectively carrying the PCV2-cap protein gene derived from porcine circle virus type 2 (PCV2), the photographs were taken under rhodamine filter in accordance with example 3 of the present disclosure.
Figure 5B:
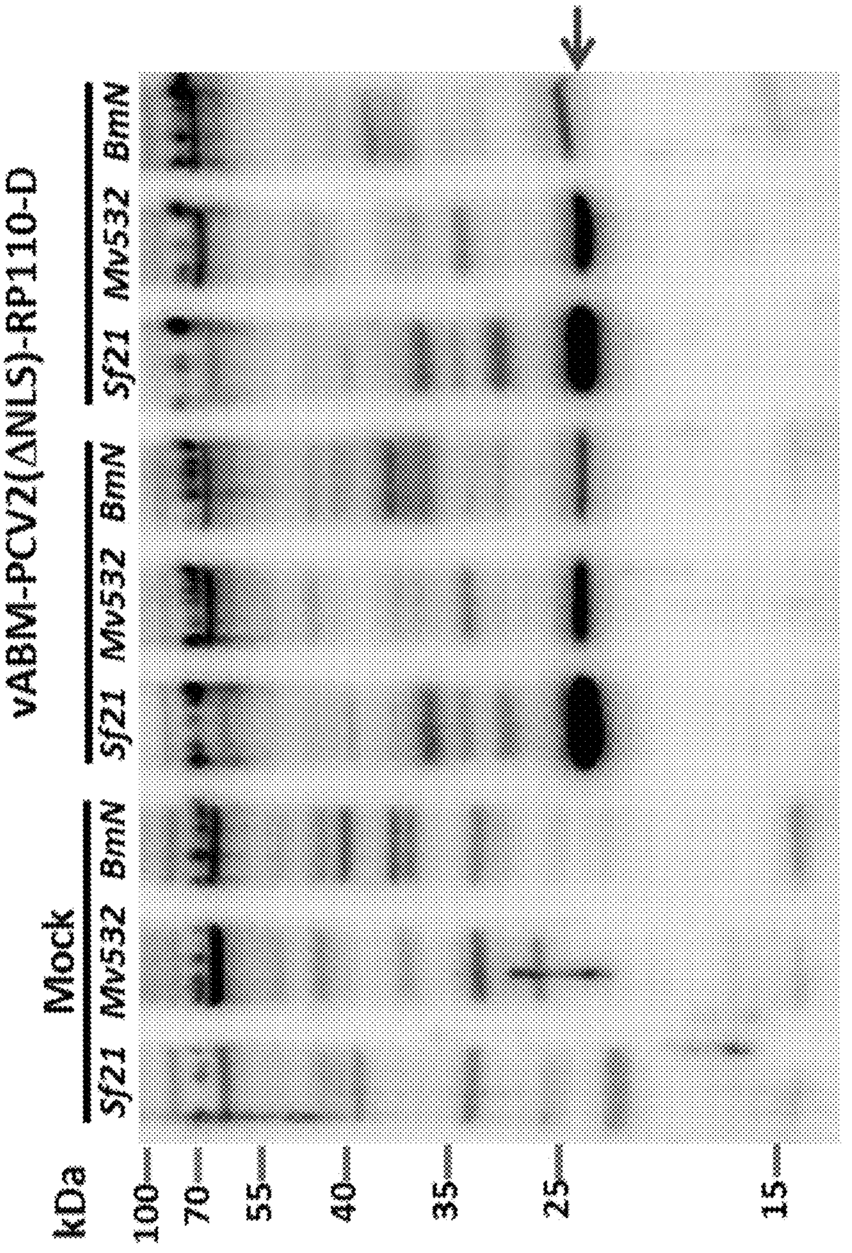
FIG. 5B is the western blot analysis of proteins respectively extracted from Sf21 cells, NTU-MV532 cells, and BmN cells infected with recombinant viruses in accordance with example 3 of the present disclosure, in which the PCV2-cap protein bands are indicated by the arrow.
Figure 5C:
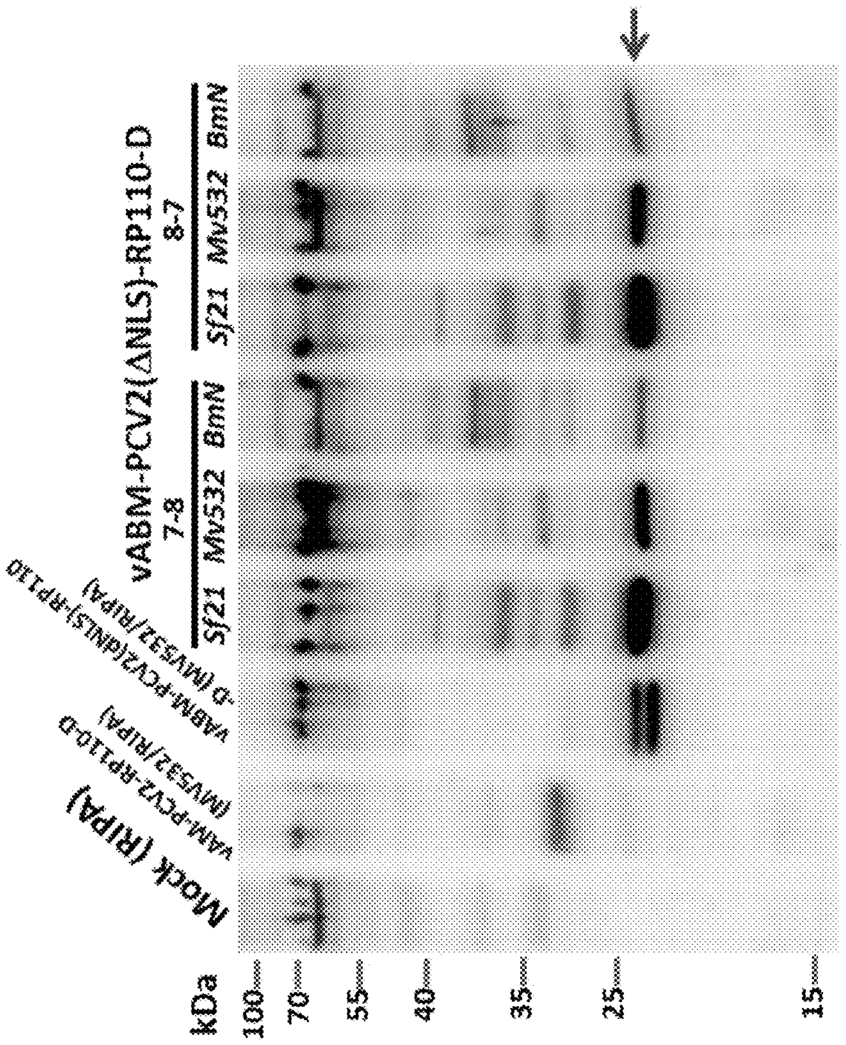

Since the hybrid AcBmMv baculovirus possesses cross host infection capability, the exogenous protein (i.e., PCV2-cap) expressed by use of the hybrid AcBmMv baculovirus/transfer vector system was further examined in all three types of host cells, including Sf21 cells, NTU-MV532 cells, and BmN cells. FIG. 5A are fluorescent photographs of Sf21, NTU-MV532, and BmN cells respectively infected with various isolated recombinant viruses containing PCV2-capgene (i.e., 5-1, 7-7, 7-8, and 8-7vABM-PCV2-RP110-D). The data indicated that 4-days post-infection, the fluorescent proteins delivered by various isolated recombinant virus of the present disclosure were detected in all three types of host cells using fluorescent microscope (view under rhodamine filter). The expression of PCV2-cap proteins in Sf21 cells, NTU-MV532 cells, and BmN cells (approximately 24 kDa, indicated by arrows) were also confirmed by the western blot analysis using anti-PCV2 antibody (FIG. 5B).

In sum, results from the foregoing working examples establish that AcMNPV based hybrid baculovirus of the present disclosure (i.e., AcBmMv) does possess cross host infection capability. Furthermore, the property of expression of exogenous protein makes the hybrid AcBmM virus a useful bio-tool or bio-insecticide to deliver genes of therapeutic or toxic proteins to be expressed in at least three different insect hosts.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An *Autographa californica* multiple nucleopolyhedrovirus (AcMNPV) based hybrid baculovirus capable of infecting different hosts comprising *Bombyx mori* nuclear polyhedrosis virus (BmNPV) genes of lef9, vlf1, p6.9, and vp80; *Maruca vitrata* multiple nucleopolyhedrovirus (MaviMNPV) genes of lef2, orf1629, and pe38; and AcMNPV/BmNPV/MaviMNPV-hybrid genes of pk1, wherein pk1 comprises the sequence of SEQ ID NO: 1, lef8, wherein lef8 comprises the sequence of SEQ ID NO: 2, DNA pol, wherein DNA pol comprises the sequence of SEQ ID NO: 3, GP41, wherein GP41 comprises the sequence of SEQ ID NO: 4, helicase, wherein helicase comprises the sequence of SEQ ID NO: 5, orf94, wherein orf94 comprises the sequence of SEQ ID NO: 6, VP1054, wherein VP1054 comprises the sequence of (SEQ ID NO: 7, orf65, wherein orf65 comprises the sequence of SEQ ID NO: 8, lef4, wherein lef4 comprises the sequence of SEQ ID NO: 9, lef5, wherein lef5 comprises the sequence of SEQ ID NO: 10, and orf99, wherein orf99 comprises the sequence of SEQ ID NO: 11.

2. The AcMNPV based hybrid baculovirus of claim 1, further comprising a first nucleic acid encoding a first fluorescent protein selected from the group consisting of green fluorescence protein (GFP), enhanced green fluorescence protein (EGFP), *Discosoma* sp. red fluorescent protein (DsRed), blue fluorescence protein (BFP), enhanced yellow fluorescent proteins (EYFP), *Anemonia magano* fluorescent protein (amFP), *Zoanthus* fluorescent protein (zFP), *Discosoma* fluorescent protein (dsFP), and *Clavularia* fluorescent protein (cFP).

3. The AcMNPV based hybrid baculovirus of claim 2, wherein the first fluorescent protein is EGFP.

4. The AcMNPV based hybrid baculovirus of claim 1, wherein the hosts are AcMNPV-permissive cells or AcMNPV-permissive insect larvae.

5. The AcMNPV based hybrid baculovirus of claim 4, wherein the AcMNPV-permissive cells are any of Sf9, Sf21, or Hi-5 cells; and the AcMNPV-permissive insect larvae are *Trichoplusia ni* or *Spodoptera frugiperda.*

6. The AcMNPV based hybrid baculovirus of claim 1, wherein the hosts are MaviMNPV-permissive cells or MaviMNPV-permissive insect larvae.

7. The AcMNPV based hybrid baculovirus of claim 6, wherein the MaviMNPV-permissive cells are NTU-MV532 cells; and the MaviMNPV-permissive insect larvae are *Maruca Vitrata.*

8. The AcMNPV based hybrid baculovirus of claim 1, wherein the hosts are BmNPV-permissive cells or BmNPV-permissive insect larvae.

9. The AcMNPV based hybrid baculovirus of claim 8, wherein the BmNPV-permissive cells are BmN cells; and the BmNPV-permissive insect larvae are *Bombyx mori.*

10. A method of producing an exogenous protein in an insect host comprising:

(a) co-transfecting a first insect host with the AcMNPV based hybrid baculovirus of claim 2 and a transfer vector to allow recombination between the AcMNPV based hybrid baculovirus of claim 2 and the transfer vector in the co-transfected first insect host, in which the transfer vector comprises in sequence, a promoter;

a second nucleic acid operably linked to the promoter and encoding the exogenous protein;

an IRES element; and a third nucleic acid operably linked to the IRES element and encoding a second fluorescent protein, wherein the first and second fluorescent proteins respectively emit a first and second fluorescence, in which the first and second fluorescence are respectively emitted at different wavelengths;

(b) isolating a recombinant virus generated from the co-transfected first insect host of step (a) that emits the second fluorescence;

(c) infecting a second insect host with the isolated recombinant virus of step (b); and (d) harvesting the exogenous protein from the infected second insect host of step (c).

11. The method of claim 10, wherein the first and second insect hosts are the same.

12. The method of claim 10, wherein the IRES element of the transfer vector is a portion of a *Rhopalosiphum padi* virus (RhPV) IRES sequence at least 90% identical to SEQ ID NO: 12.

13. The method of claim 11, wherein the first and second insect hosts are AcMNPV-permissive cells or AcMNPV-permissive insect larvae.

14. The method of claim 13, wherein the AcMNPV-permissive cells are any of Sf9, Sf21, or Hi-5 cells; and the AcMNPV-permissive insect larvae are *Trichoplusia ni* or *Spodoptera frugiperda.*

15. The method of claim 11, wherein the first and second insect hosts are MaviMNPV-permissive cells or MaviMNPV-permissive insect larvae.

16. The method of claim 15, wherein the MaviMNPV-permissive cells are NTU-MV532 cells; and the MaviMNPV-permissive insect larvae are *Maruca Vitrata.*

17. The method of claim 11, wherein the first and second insect hosts are BmNPV-permissive cells or BmNPV-permissive insect larvae.

18. The method of claim 17, wherein the BmNPV-permissive cells are BmN cells; and the BmNPV-permissive larvae are *Bombyx mori.*

19. The method of claim 10, wherein the exogenous protein is an insect toxic protein or a therapeutic protein.

* * * * *

SEQUENCE LISTING

```
<160> NUMBER OF SEQ ID NOS: 12

<210> SEQ ID NO 1
<211> LENGTH: 813
<212> TYPE: DNA
<213> ORGANISM: Baculoviridae
<220> FEATURE:
<223> OTHER INFORMATION: pk1

<400> SEQUENCE: 1

atgaccgtca acgcgtttca aacgttggca caattttacg aaaactgcaa aaatgttgaa      60

actcgctata aaataatcaa tggtcgtttt ggcaagatat ctattttatc gcacaagccc     120

actagcaaat tgtatttgca gaaaacaatt tcggcacaca actttaatgc cgacgaaata     180

aaagttcatc agttaatggg cgaccatcca aattttatcc aaatctattt taattacgga     240

tccatcaaca gccaagtgat tgtgatggac tacatagact gtcccgattt gtttgaaacg     300

ctacacataa aaggaaaact ttctcatcaa ctcgttagca atataattag acaactgtgt     360

gaagcgctca acgatttaca caagcacaat ttcgtacaca acgacataaa actcgaaaat     420

gtcttatatt tcgagttact tgatcgcgta tacgtttgcg attacggatt gtgcaaacac     480

gaaaacttac ctagcgtgca cgacggcacg ttggagtatt ttagtccgga aaaaattcga     540

cgccacaact atgcacgttc gtttgactgg tacgccgtcg gcgtgttaac gtacaagttg     600

ctaaccggcg gccgacatcc atttgaaaaa agcgaagacg aaatgttgga cttgaatagc     660

atgaagcgtc gtcagcaata caatgacatt ggtgttttaa aacacgttcg taacgttaac     720

gctcgtgact ttgtgtactg cctaacaaga tacaacctag attgtagact aacaaattac     780

aaacaaatta taaaacatga gtttttgtcg tga                                  813

<210> SEQ ID NO 2
<211> LENGTH: 2629
<212> TYPE: DNA
<213> ORGANISM: Baculoviridae
<220> FEATURE:
<223> OTHER INFORMATION: lef8

<400> SEQUENCE: 2

atgacggacg tggttcaaga tttcaacgag ttgtacgata gaattgaaaa taaatacaaa      60

ttaaaatata cttttgattg cgctacaaac agcaatgaac gtatgctttt ttgcgctatt     120
```

-continued

```
caagaacgca agtcttattt gtgttgcgct cttaatgaac agctcagttg cgtaatgcat    180
aaatgtgtgc ccgttatatt cggcacgcgc ttagacaagc aatttagaga aacggacgat    240
gtcgacgcaa acaacaatat taacggaact tttatgctgg acggcagatt tttgagtttt    300
cccaacataa tgatgaacaa caacgttttg gtgcacaatt tctacgacaa gctatacgcc    360
aaacattgca aacgcatgtt tttgtacggc aacgtggatc aagagaagca catcaatcgc    420
gcaatccaac tagtttacga caaacaagac gacgtcctgt ttgctcgaga cgtgtgctag    480
cgattacgta gtgacggaag atttaaattc tgtgctggaa acatatctgg ccaacagcgg    540
caaatggaaa ccgctcgatt ttctcttcga atacaacacg cttcacaagc aacaactcgt    600
ggaacacata aaaattatta tgaatcacga cataaactat tctatagaca gtttggccaa    660
caaaattgta tacaagcacg cctatttgct agaactgtta ttaacttcga caattttgca    720
aaactatcaa cgagttctcg acaagacggc cgacgacgac gcgtacacgg tggcgaacaa    780
gcgtcgtaaa attcaaagcg tcttgtacaa caaagagtcg aaaaagattg tcgattgtat    840
agtcaacggg cgtctcatat attgcgtatc gaaaactttt agcaagcaac gcaaagtctt    900
tcccaatcaa caggacaaca gcagcaataa caatattgaa atttcgttgc ccgtgttaaa    960
atatcgcgtc ggcaacgagg tggcgcgaat caccaacgac agcatgcgcc agaaaatgtt   1020
gaagcaaaaa aaggattttg tgaaatttat tggcagtttt tttcacggcg aaatgaccgt   1080
ggcgggcaaa aagtttttcc tttgccgcaa cgcatgtttg cccaacgtgg actacgaaat   1140
ggttgcgcaa aaatttcaat atttgctaaa acacaatctg gtcgcgttcg tggacgacct   1200
caacgacgtt caagacgact cgttgctgat cgcgtttaat gatagaccca caaatttaaa   1260
atgtttaaaa tcaaacacgt cgtttatcgt gtacactatg aaaagaaaca tggcgcccat   1320
cgaattgaag attacagaca gaatacttta cgttaatcat cacgaaggaa tgatatgcat   1380
caaaaaaaag ttgcgggtga acaacgaagc cgacattaac gtattgttga caccctacga   1440
ataccactat aaacattcta tatactataa tcccattatt cagtgtacga tcgtagaaaa   1500
cgatgacgtc aaatcgctca tgtccaagtt ggagcagtat tattatcgta attttataca   1560
tttatttcat accacgcccg tacccaaatt gattgtgtcc ctaaccaatc taaagaatgc   1620
catgcccgtg tttgagtaca aagaggaaaa ttgcgtatcg ggtttaccaa atggctactc   1680
tgtggcggta aacaagtcca ttttgctcaa caataaaatg tttaaattgt ggacgttggt   1740
gcgagacaat aaactcatga ccgccgaaga tccgtacatt ccgcacattg cgctgcccat   1800
ttgtttatac aacaacaaag tgaacaagtt gaagggcaag cttgtggtcg gccctaaaca   1860
gtcgtgttta gtaaaattta cgaatagtag cgacaaaaat tacgtcgcgc tagacgacgg   1920
acttgtgctg tacatggcag gtgtgctggt gagcaacgca aaaattaatt gggtgtacga   1980
cggccgacgg tacaaaatcg aaacgtgcac caacggcaat tttaacgttt acaaagtgta   2040
cgtttacttt agacaaatta aaaatcaaaa aattgaaaaa ctcgacgcca gcatggtggt   2100
taacggcgac aacgttatgc ttaaaatagt catagtcacg tccaccaacg atttggaagg   2160
aataaaaata tgtggcattc acggtcagaa aggtgtgttt aacggcggcg aagacctgac   2220
cgagtggatg gccgaagatg gtacgcacgc ccaaatatgc ttgtcgcccg tctcgttttt   2280
gtctcgccag tctaattttg ataaaattga gcgcaaatat gtggtgcgcg gtggaaatca   2340
cgacgacccg cacgccaagc gctatcccat cttcaacata ccatacatgc tatttaataa   2400
tacacccgac aatattttca aagaatttat taaaacaaac cacactggac acgaaaaagt   2460
```

-continued

```
cgaaggcact cgcttcgatc aatggacaaa gaatcaatcg ttcgtaggca acagaatgtc   2520

ggaaagtttg cattggatgc gcggcgggtc caacttgccg caaaactgcg gcgagtttaa   2580

cgtgatgtcc agcttgttga tgtgcaacaa tacgataatg aaaaattga              2629
```

<210> SEQ ID NO 3
<211> LENGTH: 2963
<212> TYPE: DNA
<213> ORGANISM: Baculoviridae
<220> FEATURE:
<223> OTHER INFORMATION: DNA-pol

<400> SEQUENCE: 3

```
aaatatatcc ttacaatgaa ctcaaaacgc gctttgcaga atatgcaaaa ccaggagaat     60

tcaatattac ttcagccgat acgtttcgta tcattcgttt gcattacgat gaaaaacaag    120

gttgcttgtt tgcattttgt aatacaaata tcaaagaacg agtgctgcag ttttacttta    180

aagtaaaact aaatttgtat tcttacaaac aatgctacga caagcacata tttccgtctt    240

gccgcaacaa gtgcatcagc tacaccacgt ttgtggcgcc gggcgtggaa ggaaattatt    300

tgaacaagat aaacgtgatt aaatacgaaa gaaacaaagc agcgccatcg gacaacgcga    360

tgctgttgga caagtttctt cacaacgtta atcgcgtaca catgcaaacg ccgtttgtgg    420

aaggcgccta tatgcgattc aagaaaacac aacgctgcca aaataactat gtcggtggat    480

cgacgacgcg catgtttaat ttgcaacatt ttaatgaaga ctttgagttg gtcgatgaaa    540

tgactttaac cagcggcatc atgcccgttt tgtcgtgcta tgacattgag actcattcgg    600

acggccacaa catgtcgaaa gcatcggttg attgcataat gtctatagga tttgtggtgt    660

acaaaaacga cgagtatgca aaatttttgtt ttatgtatca caagctgccg acccagattc   720

cagagaccta tgacgatgac acgtatgtgg tcatgtttca aaatgaaatc gacatgatta    780

cagcgttttt tgacatgata aaaattacaa atcccgatgt gattttggat tttaacggag    840

acgtatttga tctgccctat atacttggac gattgaataa aaccaaaatg ctattaaagc    900

gttacgattt gccggctgcg gcgccgacga caaagctgtt tataaacaag ttgggcaaca    960

aagtggacac gtattatttt aactattaca ttcacattga tttgtataaa tttttcagca   1020

gcgattctaa tcagcataaa gttgaaaact ttcaattgaa cacaatcagt agttactatt   1080

tgggtgaaaa caaaatcgat ttgccttgga ccgaaatggt caagatgtac aacactcgac   1140

ggctggacgt gattgccaag tacaacgtgc aggattgcat gttgccgcta aaattgtttg   1200

tcaaattgaa aatggccgat tctgtatatt cgcaatgtat attgcatcgt ttgtgtacag   1260

acgacgtgat atgtaatatt tcgcatttga ttagcgtggc gtgcttttac gcagccatca   1320

caaacacgcg cattaacgag agcaccggca aagaggagcc tgacccgtat ttttttaaca   1380

aaaacgatct gtcaataata tcgggccaat tcaaagccga caaagccgca gcgggtattt   1440

ctaatctcaa aagaaaattg atacctctaa aaaacatacc taaagatgcc atcaatttgg   1500

gacccgccaa tcaaacggtc aagtacaaag gcggcaaagt gttaaaacct cgtgcaggca   1560

tttacaagaa cgcgttttct ctcgatttta attctttgta cttgactata atgatagcca   1620

tttgtgcttg tttgtccaat ttaattttat gcgaagacgg caacgtgtat ttgaaccaca   1680

attcgcgtgc aatagttgtt aaattgctat taaaattgtt aagcgaaagg tgaaatttaa   1740

aaagaatcgc gaaaatcaaa gagaatcggc attcttgtac gatgtgtacg atcaaaaaca   1800

aaattccgtg aagcgcaccg ccaatagcat atacggttat tatggcattt tttacaaagt   1860

gctcgcaaac tacatcacta gagttggtcg caatcagttg cggcgggcca tttctctgat   1920
```

-continued tgaaggtttg agcaacgatc ctgagatttt aaaaaaattc aatctgaaca gcatcgggtt 1980
taaagttgtg tacggcgaca cagattctac atttgttttg cccacattta actataacga 2040
aatatttgac gaaaccgaca cattaaaaca aatatgcaca catgttgaga cacgcgttaa 2100
tagctcattt acggacggtt acaaaatggc atttgaaaat ttaatgaaag ttttaatact 2160
attaaaaaag aaaaaatatt gctatctcaa cagtgagaat aaaatcgtat acaagggttg 2220
gttagttaaa aaggatatgc ccgtttttat gagaattgcg tttaggacgg cagtggaaca 2280
aatattgcgt catttggaca taaacaaatg tttgcaaagt ttacaggcta gtttttatga 2340
atactatgat gagtttgcca aatcaaaacc gatgaccgat tacagcttta gtatgaccta 2400
taacgataac ccgggcaaaa aacgcaaatc ggctgacgat aataatgaag gtccgtcgcc 2460
caaaagacgc gtgattacgg tggctcggca ttgtagagaa attttggtta acaaaggcac 2520
ggattttgtg cccggcaacg gagatcgtat cccgtacctt ttgatagaca tcgagggcaa 2580
ggtaacagaa aaagcgtacc cgttgcgttt gttcgatcca gtaaaaatgc gaatcagctg 2640
gataaaacac atgggcattt tgtgcacatt tatgaacgag ttgcttggaa atatttggcg 2700
acgaacaaaa ggataatctt gcaaagtgtt ttaccgcaat catgcaaaag tacatgcaga 2760
atcaattgta cgatcgaaaa gaaccagtgt tagtaaaaat taaccaaaaa aaatgcggtg 2820
tcaaacgcaa acgtgacgac gacgacgaca acgacaataa tgatgatgat gatgacgatg 2880
gttgtgatag ttcagacagc gaaaatgaca ctcaatgtgc taacaatacg tataaatttt 2940
gtttgtataa aataaaaaaa taa 2963

<210> SEQ ID NO 4
<211> LENGTH: 1227
<212> TYPE: DNA
<213> ORGANISM: Baculoviridae
<220> FEATURE:
<223> OTHER INFORMATION: GP41

<400> SEQUENCE: 4
atgacagatg aacgtggcaa tttttattac aacacccctc cgccgctgag gtatccctct 60
aatccggcaa cggccatatt caccagcgcg caaacttaca acgcgcccgg gtacgtgccg 120
ccggcgacgg tgcctacgac cgtcgccacg cgcgacaaca ggatggatta cacgagccgc 180
agcaacagca caaactcggt agcgattgca ccgtacaaca agagcaaaga accgacgctc 240
gacgccggtg aatctatttg gtacaacaaa tgtgtggatt ttgttcaaaa gattattaga 300
tattacaggt gcaatgacat gtcagaactt agtcctctca tgattctttt tataaacact 360
attcgtgaca tgtgcatcga cacgaaccca atcagcgtaa acgtggtaaa gcggtttgaa 420
tcggaggaaa ccatgatacg ccacctgatt cggttgcaaa aagagttggg acagagcaac 480
gcggccgagt ccctgtcgag cgattcaaat atatttcagc catcgtttgt gctaaattcg 540
ctgccggcgt acgcgcaaaa gttttacaac ggtggcgctg atatgttggg caaagacgct 600
ttggccgagg ccgccaaaca actcagtctg gccgtccagt acatggtggc ggaagcggtg 660
acgtgcaaca ttcccattcc gttacctttc aatcagcagc tggccaaatt acatgactct 720
gttgctcaag cacgccactc tgccgccaaa catacagagc gcagtcgagt cgcgtcgctt 780
tccgcacatc aacatgataa cgatctgatc aacgccgtga ttgacgatct gtttgccggc 840
ggcggcgatt actaccacta cgtgctgaac gaaaaaaaca gggcgcgagt catgagttta 900
aaagagaacg ttgcgttttt ggcgccgcta tctgcgtctg ccaacatatt caattacatg 960

-continued

```
gccgagctgg cgacgcgagc cggcaagcaa cccagcatgt tccaaaacgc taccttccta   1020

acatcggccg ccaacgcggt caattcgcct gccgctcatt tgaccaaaaa cgcttgccag   1080

gatagcttga ccgaattggc gttccagaac gaaactctaa gacgttttat ttttcaacaa   1140

ataaattaca acaaggacgc caacgctatt attgccgcgg ccgcgcctaa cgtcactcgg   1200

ccaaacacga aaggacgcac tgtataa                                       1227


<210> SEQ ID NO 5
<211> LENGTH: 3666
<212> TYPE: DNA
<213> ORGANISM: Baculoviridae
<220> FEATURE:
<223> OTHER INFORMATION: helicase

<400> SEQUENCE: 5

atgattgaca acattttaca attttttttg aaaaacgtgc ctcaagacaa aacgtacgag     60

attaacaact tgcaagatgc aaatcattta atcattagaa acacgcgaac aggaacacgt    120

agattgtttg agtacgtcaa caactttcaa cagttcttaa acacaattag aaacaacttt    180

aacggtccgt gcgcgaaaca cgacatgggc gcatcttgcg aagacaccga agaacctgca    240

gagaaacacg cagctcaaac attagacggc cacgactggg tgttggaaag taacgatttt    300

tgcatttttg taaaaccttt cattttgaag aagcactatg acatcataca aaagtatatt    360

aattttgaag atttttttcaa gagcaccgac cctggataca ttaacaaatg cgtgcaagcg    420

ggcgattact attattggcc caactggccc aaaaagcaag ctttctcttt taacggatgg    480

cagctgtttt taaatataaa atttggaatt gtcatcgaac ccacgatacc aatcatacac    540

aacaaaaaac taggccctgt ggatttgttt gtgtttgacc ctaaatgttt tctcaacgtc    600

gagctcagcc tgcgcacgaa tcacgatccg ccgcaaacgc tgtttgtaaa tggaaaaacc    660

aagtttgacg attctcacga agacttgttt atactcaaaa tggccgacgg cactgtggcc    720

acgtgcaaag ttaatggcga gctggtcaat tcggataaaa attttttcaa ttacattagg    780

gacgacatta atttggagga atgcattacg gtgcccaagt acaagcatat cgtcaacgtc    840

aacctcaaaa gcctcagagt gttcgagaac aacaattttg acaaaaaacga cgtggacttg    900

agcgacacgc gttccagaaa accgcgcatt gtacccatta tatcggcgag cagcgaaaat    960

gcagactaca ttcaaacgca aatcaatttg gggcttatag caatttacga gaacatggtt   1020

aaagttttgg cgacccacga acaagccaac gatccaaacc ttctacaaca atactttgaa   1080

aagagcaaat ttaaaaattt tgattttttta atttacgtac tgtggaagat attgaccaag   1140

aacgaaaatt tctcgtacag agaaaccgac atcaaactgt ttttggagct tttgtgtgaa   1200

tcattatttg cctgcgacaa agaaattttg aatgaagctt tgaaacgatg tgagccttac   1260

aaaaaacaag aaaaagtagt gtttaatagg acctgcaatc attggtttga ctttgacgat   1320

accaaattgt gcgtgtcgtt gggctattat tatggcatac actacatgat atatctgact   1380

ctgtcggcta aaaacgaaac tttagatgac gatgaattgt gggcgtacac gtacgagaat   1440

gtaatggcgt taaacttgcc gcccgacatt gtgtgtaaag gattctttag aaaattagaa   1500

aacgtagtga ccggagtcaa tttggttttc aacggcaaaa actatcaaat tgtaaagaaa   1560

gaggatgacc tattcaaatt ggttaaaagc aattgttaca agttgagtaa cataaaattt   1620

aacaattgga aatacttgta cttgacaacg tacggtgtgt acaatctgtt caccaacagc   1680

tttcattcga attgtccatt tttgttgggc accacgttgc ctcagacact caagaagccc   1740

accgacgaag agtatttgcc cgaggacgcg tttaattaca tgctatctac tagcaccgac   1800
```

-continued

```
gagctcagca tttatagaat ttatcacatc gccaaaatgt gccgagatgt aaaaatgcta   1860

aaaactaaca tggccatagt taactacatg ggcaattgca acacatgcca agccgatatg   1920

cgagtcgcgt taaacaactt gtttcgcgat ttgtggaatt tggacgatga aaatttgatt   1980

acgcttgctt tgtacgtaaa caagaacaag gtttccgaca tgttgcacaa cttgaaatgt   2040

aaaccgtgtc ggtcaacggt gtcgggatct cgaccaaaat gcaaatgcta caaaaaaata   2100

aaaatcaata gaaaagcgtt aaaagtctgc ttgatagcgg acatgtttgg taacgatgca   2160

gaattgagca aattaatttg gatgctaatt tttaccaaca aaacgtacgt gtcgaccacg   2220

ttgattcgca cgaacagcga atttgttaac caacacggag agtttttttt taaagaacac   2280

aacaaaatta ttcagtactt gtatcaaaca attcacaaaa tcgaatacgt tgacatgttg   2340

atggacaagt ttaatgataa acgtttgttt ttaaccgagt tgcgcgatga tgttgcacgc   2400

gaacccgatg tccagtttga agaatcggat aacatttgca aattttacac gcaccacacc   2460

gacgcgttaa taatcctgaa aaagtacaat gtgtggtggg acaaaatcat attggcgcgc   2520

agcacggacg atttgcccac ctggttgact cgattctaca tgcgcataat catgtccaaa   2580

atggacttga aagaatactc gtacaattat ttaaaaaaga ttgtcgaagg ctatttgtac   2640

tttaaacgtt tcaccaattt taatcacgca aacgcgatta tgttgatgca tttcgccgct   2700

agtctagcca ttcccgtaga ttacggaaaa aaggctattt acatgcccgg cgaaccgggt   2760

tcgggcaagt cgtcgttttt tgagctgttg gactatttgg tgttgatgca caagtttgac   2820

gatgacaacc acagcggaga gtccaacaag gaaacgagcg acaaagaagt gagcaaactc   2880

aattcgcagc tgtacgttat caacgagttg aaacaatgca gcgaatcgta ctttaagaag   2940

catgccgatt cgagcaagag cgattccaag agcagaaaat accaagggtt gctaaagtat   3000

gaagccaact acaaaatgtt aattgttaac aacaagccgt tgtacgtgga cgattatgac   3060

gacggtgtac aagacagatt tttaattgtt tacacgaacc ataaatttgt agacagcgtt   3120

aagtttgccg gctccgtgta cgaacacatc aagtccaaac agtttccgat agaaagcatg   3180

tattacgagt cgcttgtgac gccggtgcgt ttgtttttgt cgcacgtact aatgtacaga   3240

cgcgacccca aaacgggctt tgtagtatac aaaacgctgc tgaacaacga ccctatgcat   3300

aagcacaacc taatgtgtat gagcaccaac aatagtccac tgtatgcgct catttacatt   3360

ctaaacatta aaacggtgcg caatgctact attacaatag gagaagacaa aatggaggag   3420

atgataagta ttgccgtgca gcatttgaaa aacttttttgc atccctcgtt tgttcagtac   3480

aattataaaa agaatataaa cgcaagtagt tcaaagtctt ttgtatttaa tgaacaagtt   3540

ttattacagc aaataaaaaa taaatttaaa aataattaca ataaaaccac aaatgtgttt   3600

tataacatga caatggcgtt gaacagaaac gatttgaaca ctagtgtacc aaattttgta   3660

tgttaa                                                               3666
```

<210> SEQ ID NO 6
<211> LENGTH: 372
<212> TYPE: DNA
<213> ORGANISM: Baculoviridae
<220> FEATURE:
<223> OTHER INFORMATION: orf94

<400> SEQUENCE: 6

```
atgattgctt caataaatga tatcgatgat atggacactg gcaacaacat gtcgcaagca     60

cgaagaaacc gccgcaacag gccgccagca agaccttcgg cgcaaacgca aatggcggcc    120
```

-continued gtcgacatgt tgcaaaccat caacactgcg gcctctcaaa cggctgcgtc gttgttaatc 180
aacgacatta cgcccaataa gacggaaagt ttaaaaattt tgtctactca atctgtcgga 240
gcgcgcagtc tgttggaacc gatgcaagcc aacgcgtcca caattaagtt gaatagaatc 300
gaaacggtca acgtgttaga ctttttggga agcgtttacg acaacacgat ccaagtgata 360
gttacagagt aa 372

<210> SEQ ID NO 7
<211> LENGTH: 1098
<212> TYPE: DNA
<213> ORGANISM: Baculoviridae
<220> FEATURE:
<223> OTHER INFORMATION: VP1054

<400> SEQUENCE: 7
atgtgttcga ccaagaaacc gatcaagtta gacctctgtg cctcggtgaa attaacgcct 60
ttcaaaccga tgcggccgcc caagccgatg caatgctgga tacatcctcg acgagcgaat 120
tgcaaagtaa cgcgtccacg taacaattat tcagatcccg ataacgaaaa cgacatgttg 180
cacatgaccg tgttaaacag cgtgttttta aacgagcacg caaaattgta ttatcggcac 240
ttgttgcgca acgatcaagc cgaggcgaga aaaacaattc tcaacgccga cgacgtgtac 300
gagtgcgtgt taattaaacc aattcgtacg gaacatttta gaagcgtcga cgaggctggc 360
gaacacaaca tgagcgtttt aaagatcatc atcgatacgg tcatcaagta cattggcaaa 420
ctggccgacg acgagtacat tttgatagcg gaccgcatgt atgtcgattt aatttattcc 480
gaatttaggg ccattatttt gcctcagagc gcgtacatta tcaaaggaga ttacgcagaa 540
agcgatagtg aaagcgggca aagtgtcgac gtttgtaatg aactcaaata tccttggaaa 600
ttaattacgg cgaacaattg tattgtttct acggacgagt cacgtcagtc gcaatacatt 660
tatcgcactt ttcttttgta caatacagtc ttgaccgcaa ttcttaaaca aaacaatcca 720
ttcgacgtaa ttgccgaaaa tacttctatt tcaattatag tcaggaattt gggcagctgt 780
ccaaacaata aagatcgggt aaagtgctgc gatctcaatt acggcggcat cccgccggga 840
catgtcatgt gcccgccgcg tgagattacc aaaaaggttt ttcattacgc aaagtgggtt 900
agaaacccca acaagtacaa acgatacagc gaattaattg cgcgccaatc agaagccggc 960
ggcgcatctg cgagtttacg cgaaaacgta aacaaccagc tacatgctcg agacgcgtct 1020
caattacatt tattgaattg ggaaaatttt atgggtgaat tcagcagtta ttttggtctg 1080
cacgcacaca acgtgtag 1098

<210> SEQ ID NO 8
<211> LENGTH: 807
<212> TYPE: DNA
<213> ORGANISM: Baculoviridae
<220> FEATURE:
<223> OTHER INFORMATION: orf65

<400> SEQUENCE: 8
atgaaaataa atttgtgcaa tatacaattt cagtctttaa ttaatttatt aaatttacaa 60
gcgaccacca taatgtcgct taattctaat aaaattaaag ccgatttaat acccgatgaa 120
aacgatccta aaaacgttac gttacgtctg aacagcgtgc ccgaagagtg cacggacgac 180
gacaacttct cgatagattt accattaacc acgccagagc aaaaagatga ttttatgaat 240
gccattaaac cttttgaaac tttaaatatt gaatcggata tagttaaaac caaacaaacc 300
gacgcgccgg caacaagcgg tgataataat aataatcgaa aagtggtcga tgcgaacgag 360

-continued gacgaataca cggtggacgg cttaaaactt aaatcaaaat acgtcgcgta ttacaaatgt 420
ttgaaaatac ttgtagattt tttagtaatg tacgttagca aagagaccaa catgaaagaa 480
tacgagcaag tgtacacgtt aggcagacag ttgtacgagg ttttgcgcag catttttgtc 540
gacgagccgt tcaaactgtg gctggaacgc aacacgcacg aatttgacaa caataaagac 600
aaaattttag aaactttaca gagcgaattg aaacttgcgt tggccgataa ggacaaattg 660
aaaacgtgca cgttcaaaga tatcatcacc aatttgttga acacgaaatt ggattgcaaa 720
tacgattgcg ccgacgagta tattaagccg aattgtatag tggacacgta caattgttgc 780
aatttagttt tcaaaaaaga aacatga 807

<210> SEQ ID NO 9
<211> LENGTH: 1398
<212> TYPE: DNA
<213> ORGANISM: Baculoviridae
<220> FEATURE:
<223> OTHER INFORMATION: lef4

<400> SEQUENCE: 9
atggactacg gcgattttgt gattgagaaa gaaatctctt attcaataaa ttttagccaa 60
gatttgttgt ataaaatttt aaattcttat attgttccta attattcgct ggcacaacaa 120
tatttcgatt tgtacgacga aaacggcttt cgcactcgta tacctattca gagcgcttgc 180
aataacataa tatcaagcgt gaaaaagact aattccaaac acaaaaaatt tgtttattgg 240
cctaaagata ccaacgcgtt ggtgccgttg gtgtggagag agagcaaaga aatcaaactg 300
ccttacaaga ctctttcgca caacttgagt aaaataatta aagtgtacgt ttaccaacac 360
gataaaattg aaatcaaatt tgaacatgta tatttttcga aaagtgacat cgatttattt 420
gattccacga tggctaacaa gatatccaaa ctgctgactt tgttggaaaa tggaaacgct 480
tcatcggaga cgctgcaaaa ctcgcaagtg ggcagcgatg aaattttggc ccgcatacgt 540
ctcgaatatg aatttgacga cgacgcgccc gacgacgcgc agctaaacgt gatgcaacat 600
aattgcagac atggaagcgt tgaccgacgc gcaaaacata tcaccgttcg tgccgctgac 660
cacgttgatt gacaagatgg cccctcgaaa atttgaacat gaacaaaaaa tagtgtacgg 720
agacgacgcg ttcgacaacg cgtccgtaaa aaaatgggcg ctcaaattgg acggtatgcg 780
gggcagaggt ctgtttatgc gcaatttttg cattattcaa accgacgcga tatgcaattc 840
tacaaaacca aaatggccaa tctgttttcg ctaaacaaca ttgtggcctt tcaatgtgag 900
gttatggaca aacaaaagat ttacattaca gatttgttgc aagtgtttaa atacaaatac 960
aacaatcgaa cacagtacga gtgcggcgtg aacgcgtcat acgctataga tccggtgacg 1020
gccatcgaat gtataaacta catgaacagc aacgtgcaaa gcgtcacgtt gaccgacact 1080
tgccccgaaa ttgaattgag gtttcagcaa tttttgatc cgccgctaca gcagagcgat 1140
tacatgaccg tgtccgtgga cgggtatgtc gtgctcgaca ccgagttgag atacgtcaaa 1200
tataaatgga tgccaacaac cgagttggag tatgacgccg tgaataactc gtttaacaca 1260
ctcaatgggc cattgaacgg tctcgtgatt ttaaccaact tgccggagtt gctgcacgaa 1320
aacatttacg aatgtgtgat cgcggacacg acaataaacg tgttgaaaca tcgtcgcgac 1380
cgaatcgtgc caaattaa 1398

<210> SEQ ID NO 10
<211> LENGTH: 798
<212> TYPE: DNA

-continued

```
<213> ORGANISM: Baculoviridae
<220> FEATURE:
<223> OTHER INFORMATION: lef5

<400> SEQUENCE: 10

atgtcgtttg atgatggcgt cgttaaggcg caaacagatc catttgcttt gaagcgagga     60

ggccataatg tacaaaaatg gaccagttac gccttattta aactgtttaa agagtttcgt    120

ataaacaaaa actactctaa actaatagat ttcttaacag aaaattttcc caacaacgtc    180

aaaaacaaaa cgttcaactt ttcgtctacc ggccatctgt ttcactcgtt gcacgcgtac    240

gtgcccagcg tcagtgattt ggtgaaagag cgcaaacaaa ttcgattgca gacagaatat    300

ttggcaaagc tgttcaacaa cacaataaac gatttcaaac tgtacactga attgtacgag    360

tttatcgaac ggaccgaagg cgtcgattgc tgttgtccgt gccagctatt gcacaagagt    420

ctatttaaca cgaaaaatta cgtaaaaacc ctaaattgta aactgtttga cataaagccg    480

cccaaattta aaaaggaacc tttcgacaat attctttaca agtattccct aaattacaaa    540

agtttattgt tgaaaaaaaa ggaaaagcat accaacactg ggtgtacgcg caaaaagaaa    600

atcaaacaca gacagatatt gaatgataaa gttatttatt tacaaaacag taataaaaat    660

aaactatttg agcttagcgg gcttagttta aaatcttgca gacacgattt tgtaacagtc    720

gaaagccaaa cgagggcagg cgacgaaatc gcttcgttcc ttcgctactg tcggatgtgt    780

ggaatgtctg gctgttaa                                                  798


<210> SEQ ID NO 11
<211> LENGTH: 317
<212> TYPE: DNA
<213> ORGANISM: Baculoviridae
<220> FEATURE:
<223> OTHER INFORMATION: orf99

<400> SEQUENCE: 11

atgaaaccga cggcggccga cattatatcg agagcgacag gcggtcgcgc cggcaacaat     60

atcgtcgaca tcatccaagc ccacaactcg ccgactgaag gcgatcagct cggccaattt    120

gtaaatagaa accgatcgct aattaaagaa tttgttttag tagtgtgcgg gtttttaatt    180

tttgttatga ttgtgttatt ctttatgtta ttggttgtga tcttgttaaa ccaagaaaca    240

gttactgtac aaaaataaaa tatgaaacta ctttattaga aaattatgat attagaaata    300

gaaatgcaac aacataa                                                   317


<210> SEQ ID NO 12
<211> LENGTH: 110
<212> TYPE: DNA
<213> ORGANISM: Rhopalosiphum padi
<220> FEATURE:
<223> OTHER INFORMATION: Rhopalosiphum padi virus 5'-UTR

<400> SEQUENCE: 12

agttaaagct ttataactat aagtaagccg tgccgaaacg ttaatcggtc gctagttgcg     60

taacaactgt tagtttaatt ttccaaaatt tatttttcac aatttttagt               110
```